United States Patent
Biadillah et al.

(10) Patent No.: US 9,226,788 B2
(45) Date of Patent: *Jan. 5, 2016

(54) FENESTRATION THROUGH FOREIGN MATERIAL

(71) Applicant: Baylis Medical Company Inc., Mississauga (CA)

(72) Inventors: Youssef Biadillah, Lausanne (CH); Amanda Hartley, Caledon (CA); Gareth Davies, Toronto (CA); Naheed Visram, Epsom (GB); Taras Juzkiw, Mississauga (CA)

(73) Assignee: BAYLIS MEDICAL COMPANY INC., Montreal, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,468

(22) Filed: Dec. 9, 2013

(65) Prior Publication Data

US 2014/0100560 A1   Apr. 10, 2014

Related U.S. Application Data

(63) Continuation of application No. 13/286,041, filed on Oct. 31, 2011, now Pat. No. 8,623,005, which is a continuation-in-part of application No. 11/905,448, filed on Oct. 1, 2007, now Pat. No. 8,048,071.

(60) Provisional application No. 60/827,466, filed on Sep. 29, 2006, provisional application No. 61/448,578, filed on Mar. 2, 2011.

(51) Int. Cl.
*A61B 18/18* (2006.01)
*A61B 18/04* (2006.01)
*A61B 18/14* (2006.01)

(Continued)

(52) U.S. Cl.
CPC ............. *A61B 18/04* (2013.01); *A61B 18/1492* (2013.01); *A61B 8/12* (2013.01); *A61B 2018/00083* (2013.01); *A61B 2018/00214* (2013.01); *A61B 2018/00702* (2013.01); *A61B 2018/00827* (2013.01);

(Continued)

(58) Field of Classification Search
CPC ...... A61B 18/1492; A61B 18/04; A61B 8/12; A61B 2018/0083; A61B 2018/00214; A61B 2018/00827; A61B 2018/00875; A61B 2018/00898; A61B 2019/5466; A61B 2018/00702
USPC ...................................... 606/20–52, 167, 170
See application file for complete search history.

(56) References Cited

U.S. PATENT DOCUMENTS

| 6,562,031 B2 * | 5/2003 | Chandrasekaran et al. .... 606/41 |
| 7,828,796 B2 * | 11/2010 | Wong et al. ..................... 606/45 |
| 2007/0066975 A1 * | 3/2007 | Wong et al. ..................... 606/45 |

*Primary Examiner* — Joseph Stoklosa
*Assistant Examiner* — Amanda Scott
(74) *Attorney, Agent, or Firm* — Nir Lifshitz; Glenn Arnold

(57) ABSTRACT

Described herein is a method for creating a channel through a foreign material located in a body of a patient. The foreign material defines a material first surface and a substantially opposed material second surface and the channel extends through the foreign material between the material first and second surfaces. The method uses an apparatus including an electrode, and includes the steps of: positioning the electrode substantially adjacent to the material first surface; energizing the electrode with a radiofrequency current; and using the electrode energized with the radiofrequency current to deliver energy into the foreign material to create the channel. In some embodiments, the patient's body includes a heart defining a septum, the septum defines an aperture extending therethrough and the foreign material extends across the aperture to cover the aperture.

21 Claims, 14 Drawing Sheets

(51) Int. Cl.
*A61B 8/12* (2006.01)
*A61B 18/00* (2006.01)
*A61B 19/00* (2006.01)

(52) U.S. Cl.
CPC ................. *A61B 2018/00875* (2013.01); *A61B 2018/00898* (2013.01); *A61B 2019/5466* (2013.01)

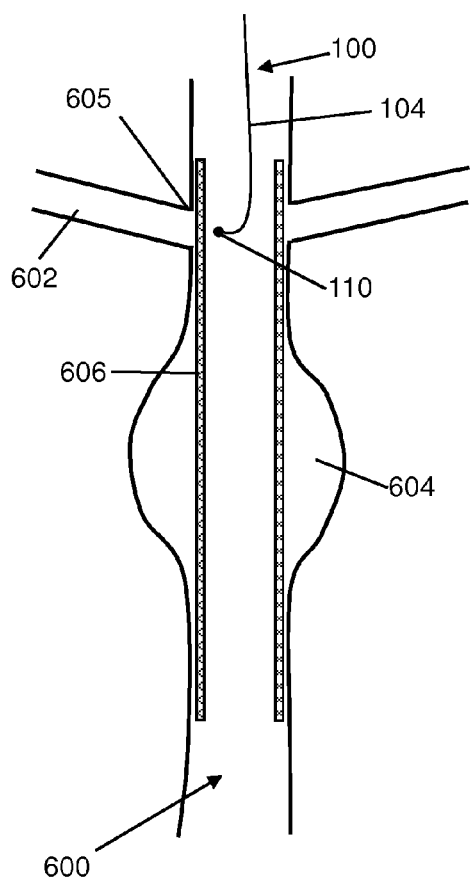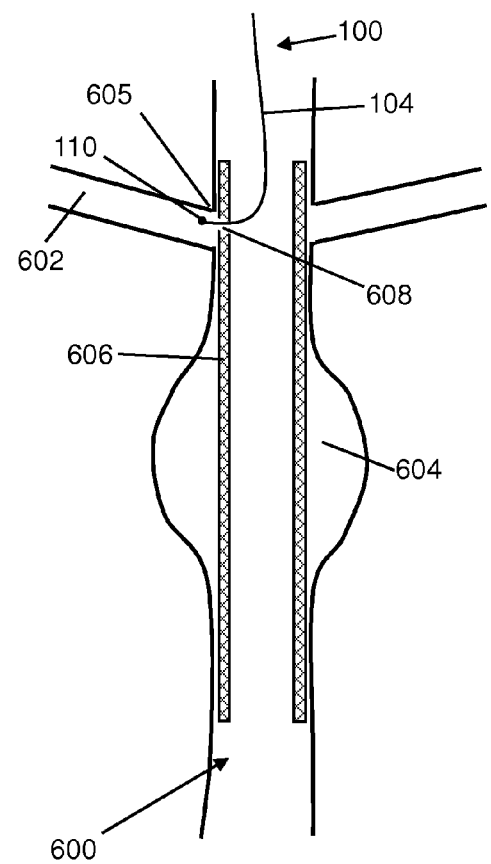
Figure 6A                    Figure 6B

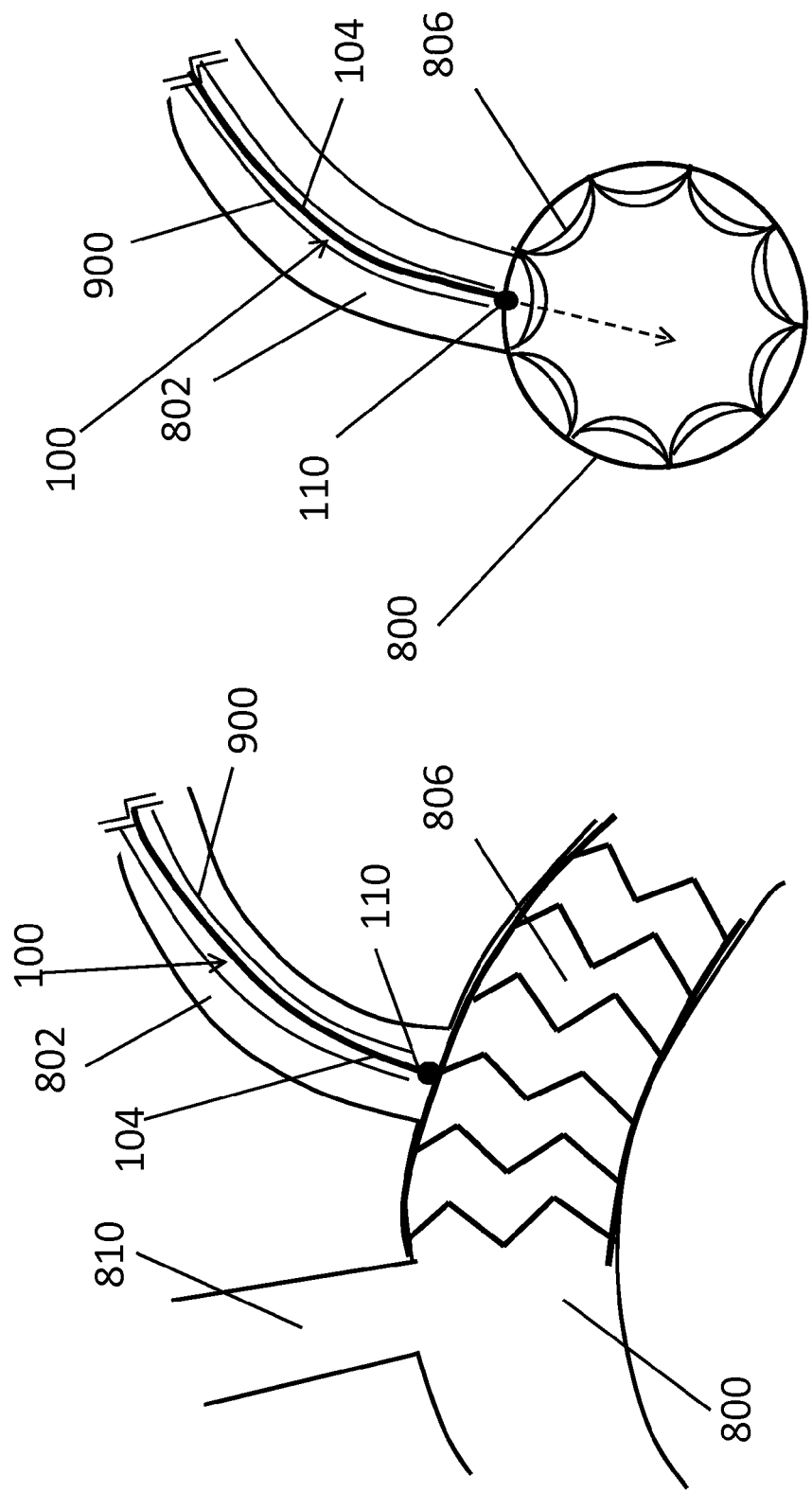

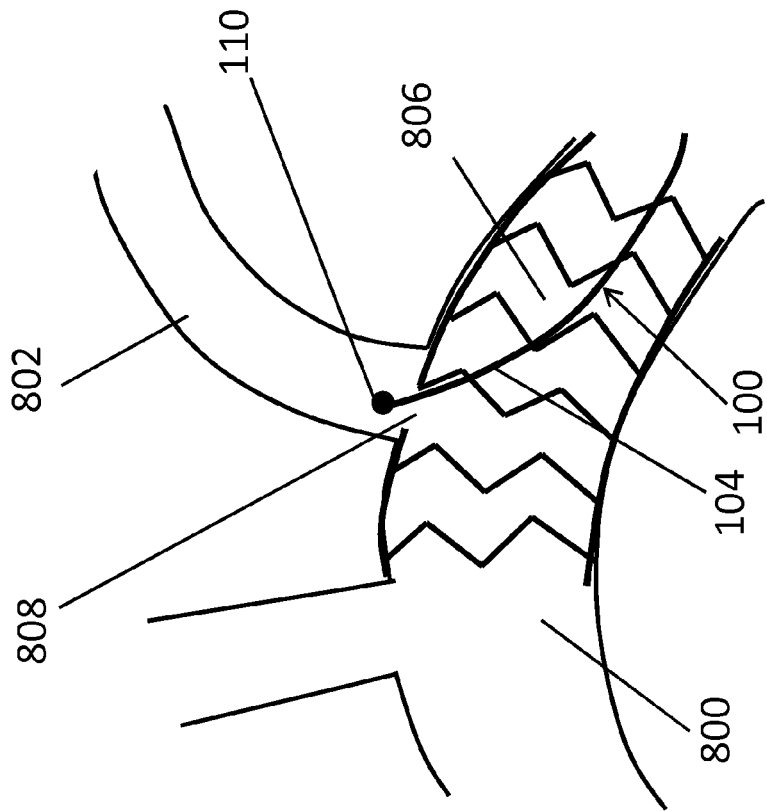
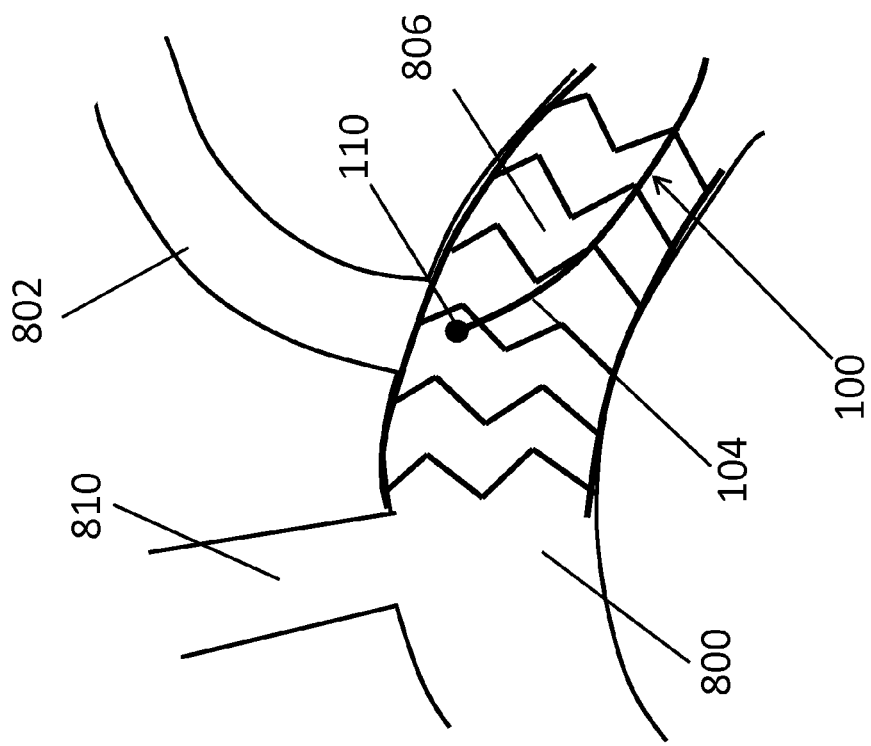

FENESTRATION THROUGH FOREIGN MATERIAL

CROSS-REFERENCES TO RELATED APPLICATIONS

This application is a continuation of U.S. patent application Ser. No. 13/286,041, filed on 31 Oct. 2011, which is a continuation-in-part of U.S. patent application Ser. No. 11/905,448, filed on Oct. 1, 2007, now U.S. Pat. No. 8,048,071, which claims the benefit of U.S. provisional patent application Ser. No. 60/827,466 filed on 29 Sep. 2006. U.S. patent application Ser. No. 13/286,041 further claims the benefit of U.S. provisional application No. 61/448,578, filed on Mar. 2, 2011. All of these US patent applications and provisional patent applications are hereby incorporated by reference in their entirety.

FIELD OF THE INVENTION

The present invention relates generally to methods and devices usable to deliver energy within the body of a patient. More specifically, the present invention is concerned with a method for creating a channel through foreign material.

SUMMARY OF THE INVENTION

In contrast to the commonly understood mechanisms of radiofrequency perforation, it has been unexpectedly found that, as described further herein below, a radiofrequency-based apparatus is usable to create channels through foreign materials which may be, for example, substantially synthetic materials. An embodiment of a proposed method of a present invention is used to create a channel within foreign material that extends across an aperture defined by the septum of the heart of a patient.

In one broad aspect, embodiments of the present invention provide a method for creating a channel through a foreign material located in a body of a patient, said foreign material defining a material first surface and a substantially opposed material second surface, said channel extending through said foreign material between said material first and second surfaces, said method using an apparatus including an electrode, said method comprising: positioning said electrode substantially adjacent to said material first surface; energizing said electrode with a radiofrequency current; and using said electrode energized with said radiofrequency current to deliver energy into said foreign material to create said channel; wherein said body includes a heart defining a septum, said septum comprising an aperture extending there-through and wherein said foreign material extends across the aperture to cover the aperture.

As feature of this broad aspect, the foreign material is included in a septal patch that covers the aperture. As an example of this feature, the septal patch extends in a plane outside of the septum. As another example of this feature, the septal patch extends inside the aperture.

As another feature of this broad aspect, the septum comprises an atrial septum. As an alternative feature of this broad aspect, the septum comprises a ventricular septum.

As still another feature of this broad aspect said foreign material includes a material selected from the group consisting of polyethylene terephthalate (PET), a cotton, a polyester material and fabrics thereof. As an example of this feature, said foreign material includes a synthetic material. In some embodiments the synthetic material comprises a polyester material.

As another feature of this broad aspect thermal energy is transferred from said electrode upon said electrode being energized with said radiofrequency current to substantially melt said foreign material adjacent said electrode, thereby creating a channel through said foreign material, wherein said electrode is heated to a temperature that is substantially larger than a melting temperature of said foreign material.

In accordance with another broad aspect, some embodiments of the present invention provide a method of gaining access into a left side of a heart, the heart having a septum defining an aperture, wherein foreign material extends across the aperture, said method using an apparatus including an electrode, said method comprising: positioning said electrode substantially adjacent to said foreign material; and creating a channel within said foreign material using said electrode energized with said radiofrequency current to deliver energy into said foreign material to allow the apparatus to be advanced through the channel thereby crossing the septum to be positioned into the left side of the heart.

As a feature of this broad aspect, the step of positioning said electrode further comprises gaining access into the heart via an inferior vena cava.

As another feature of this broad aspect, the step of positioning said electrode further comprises gaining access into the heart via a superior vena cava.

In another broad aspect embodiments of the present invention provide a method for creating a channel through a foreign material located in a body of a patient, said foreign material defining a material first surface and a substantially opposed material second surface, said channel extending through said foreign material between said material first and second surfaces, said method using an apparatus including an electrode, said method comprising: positioning said electrode substantially adjacent to said material first surface; energizing said electrode with a radiofrequency current; using said electrode energized with said radiofrequency current to deliver energy into said foreign material to create said channel; assessing a composition of a material in contact with said apparatus; and, upon determining that said electrode is positioned adjacent a metallic structure, repositioning the apparatus away from said metallic structure.

As a feature of this broad aspect the step of assessing the composition comprises obtaining tactile feedback.

As another feature of this broad aspect of this feature the step of assessing the composition comprises measuring one or more parameters substantially while delivering energy.

As still another feature of this broad aspect, the steps of assessing and repositioning the apparatus comprise: measuring an impedance of the material in contact with said apparatus; determining if the measured impedance indicates that said apparatus is in contact with a metallic structure; and repositioning the apparatus upon determining that said apparatus is in contact with a metallic structure while repeating the steps of measuring and determining, until an impedance is recorded indicating said apparatus is positioned away from said metallic structure.

As an example of this feature, the impedance is measured substantially continuously during energy delivery.

As another example of this feature, the impedance is measured at predetermined intervals during energy delivery.

As still another example of this feature, the delivery of energy is changed based on a change in the measured impedance.

As a further example of this feature, the delivery of energy is stopped prior to repositioning the apparatus.

BRIEF DESCRIPTION OF THE DRAWINGS

In the appended drawings:

FIGS. 6A and 6B, in schematic views, illustrate a method for creating a channel in a stent graft extending across an ostium of a renal artery of a patient in accordance with an embodiment of the present invention;

FIGS. 8A and 8B, in schematic views illustrate a method for creating a channel in a stent graft extending across an ostium of a left Subclavian Artery (LSA) of a patient in accordance with an alternative embodiment of the present invention;

FIG. 8C is a right anterior oblique view illustrating a method for creating a channel in a stent graft extending across an ostium of a left Subclavian Artery (LSA) of a patient in accordance with an alternative embodiment of the present invention;

FIGS. 9A and 9B, in schematic view illustrates a method for creating a channel in a stent graft extending across an ostium of a left Subclavian Artery (LSA) of a patient in accordance with an alternative embodiment of the present invention.

DETAILED DESCRIPTION

Figure 1A:
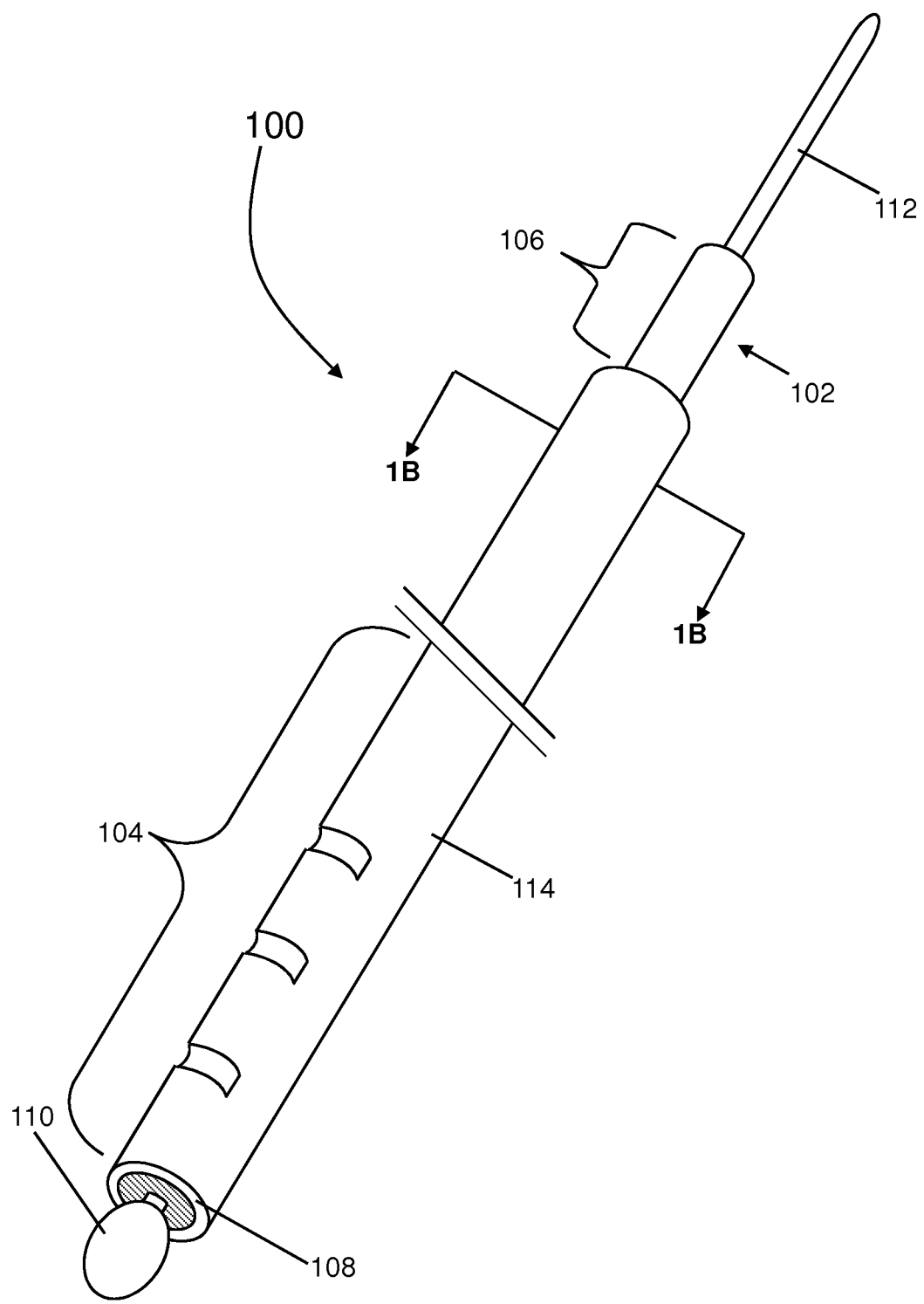
FIG. 1A, in a perspective view, illustrates an apparatus for creating a channel through a foreign material in accordance with an embodiment of the present invention.

Generally speaking, the proposed method is performed for creating a channel through foreign material located in a body of a patient. The foreign material defines a material first surface and a substantially opposed material second surface and the channel extends through the foreign material between the material first and second surfaces. Typically, the method uses an apparatus including a substantially elongated member defining a proximal end region and a substantially longitudinally opposed distal end region, the substantially elongated member including an electrode located about the distal end region.

The method includes positioning the electrode substantially adjacent to the material first surface; energizing the electrode with a radiofrequency current; and using the electrode energized with the radiofrequency current to deliver energy into the foreign material to create the channel.

For example, the method is usable for restoring blood flow to a blood vessel of a body of a human or animal, the blood vessel being occluded by a foreign material. In this case, the channel is created through the foreign material.

As a feature of the aforementioned aspects, in some embodiments of the invention, the apparatus has a substantially atraumatic distal end, thus reducing the risk of unintentional perforation of a body vessel or other tissues. Also, the use of energy in creating the channel allows for the creation of channels in foreign materials through which creation of such channels is difficult, if not impossible, to perform using mechanical force. In some embodiments, the method is performed using relatively small apparatuses, for example apparatuses having a relatively small diameter, which are therefore relatively easily introduced into relatively small vessels.

With specific reference now to the drawings in detail, it is stressed that the particulars shown are by way of example and for purposes of illustrative discussion of embodiments of the present invention only, and that many alternative embodiments of the invention are within the scope of the appended claims.

For the purposes of this description, the term 'proximal' indicates next to or nearer to the user, and the term 'distal' indicates further away from the user, when the apparatus is in use.

APPARATUS

Structure

As illustrated in FIG. 1, one embodiment of an apparatus 100 according to the present invention includes a substantially elongated member 102 defining a distal end region 104 and a proximal end region 106. The distal end region 104 includes a distal tip 108 and an electrode 110 located about the distal end region 104. The electrode 110 is usable as a radiofrequency energy delivery component. In the embodiment shown in FIG. 1, the apparatus 100 further comprises an actuator 112 for directing at least a portion of the distal end region 104 in a desired direction.

The elongated member 102 may be electrically conductive and may be operable to conduct electrical energy to the distal tip 108, and more specifically to the electrode 110. In such embodiments, the elongated member 102 is also known as as a core wire. In the illustrated embodiments, the elongated member 102 is at least partially covered with an insulating material 114 for substantially preventing conduction of electrical energy to surrounding bodily tissue. In accordance with these embodiments, the insulating material 114 may be made of any of a variety of electrically insulating materials and may have any suitable thickness, provided that the elongated member 102 is at least partially electrically insulated. In one particular embodiment, the insulating material 114 is at least about 0.1 mm thick. The elongated member 102 may comprise a wire that is narrow enough to be navigated through a blood vessel. In some specific embodiments, the elongated member 102 measures about 0.2 mm to about 1.0 mm in diameter.

In alternative embodiments, the insulating material 114 is discontinuous at one or more locations along the elongated member 102. For example, in one such embodiment, a number of discontinuities in the insulating material 114, along the length of the elongated member 102, create a 'banded' appearance, wherein insulated regions are interleaved between electrically exposed and conductive regions. In another embodiment, a region of the insulating material 114 does not completely circumscribe the elongated member 102. For example, insulating material 114 may traverse approximately 180 degrees of the circumference of the elongated member 102, leaving the remaining area electrically exposed. Any shape or pattern of discontinuities may be present and the invention is not intended to be limited in this regard. Discontinuities in the insulating material 114 may affect the distribution of energy, for example current density, around the elongated member 102 when the elongated member 102 is used to deliver energy. Embodiments of the present invention comprising such discontinuities may be suitable for specific applications, for example, when it is desirable to deliver energy along a portion of the length of the elongated member 102 or to focus the delivery of energy to a particular location or target site. In some embodiments, discontinuities in the insulating material 114 correspond, at least in part, to discontinuities in the structure of the elongated member 102. For example, in one specific embodiment, notches, described in greater detail below, are present in the elongated member 102, the thickness of the insulating material 114 being reduced in the vicinity of the notches.

In some embodiments, at least a portion of the proximal end region 106 of the elongated member 102 is electrically exposed, such that the elongated member 102 may be electrically coupled to an energy source, for example using an electrical connector.

In alternative embodiments, the elongated member 102 is made out of an electrically insulating material. In such embodiments, the insulating material 114 is typically not required. For example, in some embodiments, the elongated member 102 is made out of nylon (e.g. Pebax), polyetheretherketone (PEEK), or polypropylene, and at least one electrode 110 is attached to the distal tip 108, the electrode 110 being electrically couplable to an energy source. In one particular embodiment, the electrode 110 is electrically coupled to the actuator 112, which itself may be made of an electrically conductive material and which may be capable of being electrically coupled to an energy source. Alternatively, one or more electrodes 110 are attached to the elongated member 102, rather than to the actuator 112.

Figure 2:
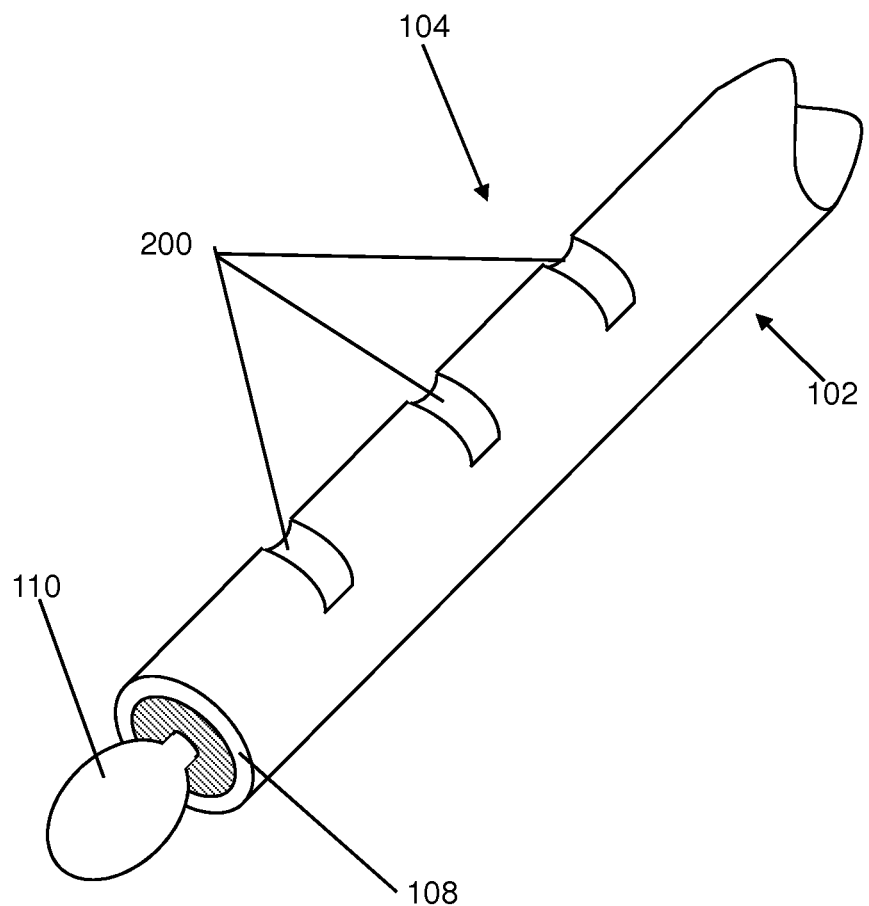
FIG. 2, in a partial perspective view, illustrates a distal end region of the apparatus of FIG. 1A.

In some embodiments, at least a portion of the distal end region 104 is structured to prevent unwanted damage to a body vasculature of a patient when the apparatus 100 is inserted therethrough. For example, as shown in FIG. 2, the distal tip 108 may have a substantially atraumatic shape, for example having a blunt or rounded edge, for preventing such damage as the apparatus 100 is maneuvered through the body vasculature. In other embodiments, the distal tip 108 may be substantially semispherical, hemispherical, spherical or flattened, or may have any other shape that is unlikely to damage tissues upon contact. Alternatively or in addition, in some embodiments, at least a portion of the distal end region 104 of the elongated member 102 has a reduced rigidity relatively to the proximal end region 106. The reduced rigidity may serve to further decrease the ability of the elongated member 102 to puncture tissue, for example the tissue of a vessel wall, with the application of mechanical force. This reduced rigidity may be achieved by, for example, by the inclusion or substitution of a different material in the manufacture of the elongated member 102, by reducing the amount of material present in at least a portion of the distal end region 104, or by reducing the diameter of the actuator 112. Material may be removed, for example, by using a latticework or other discontinuous structural framework, or alternatively by thinning the wall of a portion of the elongated member 102.

Figure 1B:
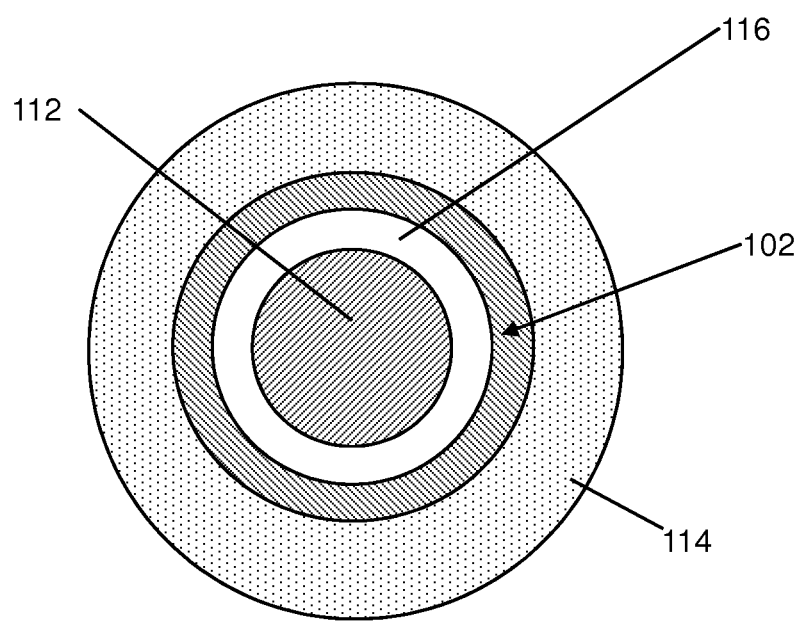
FIG. 1B, in a front cross-sectional view taken along the line 1B-1B of FIG. 1A, illustrates the apparatus of FIG. 1A.

In some embodiments, as seen in FIG. 1B, the elongated member 102 defines a lumen 116, as will be described further herein below, and the wall thickness of the elongated member 102 tapers in the portion of distal end region 104 approaching the distal tip 108. For example, the elongated member 102 may taper from inside to outside, thereby maintaining a consistent outer diameter and having a changing inner diameter. Alternatively, the elongated member 102 may taper from outside to inside, thereby maintaining a consistent inner diameter and having a changing outer diameter, or from both the inside and the outside thereby having the outer diameter decrease and the inner diameter increase.

As has been mentioned above, the apparatus 100, as shown in the illustrated embodiments, includes an electrode 110 located about the distal end region 104. The electrode 110 may be integral with one or both of the elongated member 102 and the actuator 112 or may be otherwise attached to the distal tip 108. For example, the distal tip 108 may be covered with an electrically conductive cap, the cap thus forming the electrode 110. In embodiments wherein the electrode 110 is not integral with one or both of the elongated member 102 and actuator 112, the electrode 110 may be otherwise electrically coupled to one or both of the elongated member 102 and actuator 112 or to another wire operable to electrically couple electrode 110 to an energy source. For example, in one embodiment, the electrode 110 is integral with the actuator 112 and may be associated with the distal tip 108 by being passed through the elongated member 102. Alternatively, when the apparatus 100 comprises a core wire, as described hereinabove, the electrode 110 may be integral with the core wire.

The electrode 110 may be larger or smaller, or may have the same diameter, as the distal tip 108. In some embodiments, the electrode 110 is sized to be operable to generate sufficient heat to create the channel in the foreign material, when energy is supplied to the electrode at a sufficient power level. In the context of the present invention, the term foreign material encompasses any material foreign to the body being treated including synthetic materials. In one specific embodiment, the electrode may measure from about 0.40 mm to about 0.43 mm in diameter and from about 1.2 mm to about 1.5 mm in length.

In the embodiment shown in FIG. 1B, as has been mentioned above, the elongated member 102 defines a lumen 116 extending at least partially therethrough. FIG. 1B shows one embodiment of a centrally located substantially circular lumen 116 defined by the elongated member 102. In alternative embodiments, the lumen 116 has any other suitable alternative shape and size and may be eccentrically located through the elongated member 102. In other embodiments that do not comprise the lumen 116, the elongated member 102 is a substantially solid structure. The lumen 116 may be sized to receive the actuator 112 therein, as shown in FIG. 1. For example, in some embodiments, the lumen 116 is large enough to receive the actuator 112, but is not large enough to accommodate other wires, sensors, or the passage of fluid. In further embodiments, the lumen 116 is sized to receive the actuator 112 along with one or more wires but is still not be large enough to accommodate fluid flow. In one specific embodiment, the lumen 116 measures about 0.1 mm to about 1.0 mm in diameter. The flexibility of the elongated member 102 may be dependent, in part, on the wall thickness of the elongated member 102, between an inner diameter defined by the lumen 116 and an outer diameter. In one particular embodiment, the elongated member 102 has a wall thickness measuring about 0.01 mm to about 0.2 mm. The flexibility of the elongated member 102 is also dependant on the outer diameter of the elongated member 102. In some embodiments, the elongated member 102 has a beam strength of at least 0.001 lbf as measured by the ASTM E855-90 3-point bent test.

In the embodiment illustrated in FIGS. 1A, 1B and 2, the actuator 112 is operable to direct at least a portion of the distal end region 104 in a desired direction. In one embodiment, the actuator 112 comprises a single pull-wire disposed within the lumen 116 of the elongated member 102 and attached to at least one point in the distal end region 104 of the elongated member 102. For example, the actuator 112 may be attached to the distal end region 104 at or adjacent to the distal tip 108. The actuator 112 may be relatively thin, in some embodiments, in order to allow the inner diameter of the elongated member 102 to be reduced, thus potentially reducing the diameter of the apparatus 100 as a whole. In one particular embodiment, the actuator 112 measures from about 0.03 mm to about 0.30 mm in diameter.

The actuator 112 may be attached to the elongated member 102 such that manipulation of the actuator 112 via the application of mechanical energy to transmit tension along the length of the actuator 112 may effect a change in the elongated member 102. For example, in some embodiments, manipulation of the actuator 112 may cause at least a portion of the elongated member 102 to change shape. Such a change of shape may involve the adoption of a bent configuration, wherein, the term "bent" is defined to mean having a deviation from a straight line; this may take the form of a rigid bend or a subtler curve, with one or more angles of curvature. In other embodiments, this change of shape may involve a compression, or accordion-like collapsing of the elongated member 102, wherein one or more sections of the elongated member 102 fold or bend backwards. Such an effect may cause the position of the distal tip 108 to change, without necessarily inducing any deviation of the distal tip 108 away from the longitudinal axis of the distal end region 104 (i.e. the distal tip 108 may still point in its original direction).

In other embodiments of the present invention, the apparatus 100 may comprise other means for directing at least a portion of the distal end region 104 in a desired direction. For example, the apparatus 100 may comprise one or more electro-magnetic, piezoelectric or hydraulic mechanisms for changing the shape of the elongated member 102. In one such embodiment, the apparatus 100 may comprise at least one magnetically responsive element, which may assist in guiding the apparatus 100 to a desired direction upon the application of a magnetic field.

In some embodiments, the apparatus 100 includes a preformed curved section. In such embodiments, the distal tip 108 may be directed in a desired direction by applying torque to the proximal end region 106. In such embodiments, an actuator may not be required.

With respect now to the embodiment shown in FIG. 2, the distal end region 104 of the elongated member 102 may contain one or more notches 200 to aid in a change of shape of the elongated member 102 when tension is applied through the actuator 112. For the purposes of this description, the notches 200 may be any regions wherein discontinuities are present in the wall of the elongated member 102. In some embodiments, the notches 200 comprise scores, cuts, or other discontinuities in either the inner or outer surface of the wall of the elongated member 102 that do not completely traverse the circumference of the elongated member 102. In alternative embodiments, the notches 200 comprise regions wherein entire sections of the wall of the elongated member 102 are absent. In one specific example, as shown in FIG. 2, one or more sections of the wall of the elongated member 102, each section extending at least 180 degrees around the circumference of the elongated member 102, are absent, which may result in a toothed or serrated appearance. Notches 200 are present, for example, along about 5 mm to about 50 mm of the length of the elongated member 102. The notches 200 may be regularly or irregularly spaced, identically, similarly or dissimilarly sized, oriented at any angle with respect to the elongated member 102 and may lie at any suitable angles along the elongated member 102. The notches 200 may have abrupt edges or may comprise regions where the thickness of a wall of the elongated member 102 changes gradually to create a discontinuity.

In other embodiments, the notches 200 comprise regions composed of a material different than that of the surrounding body of the elongated member 102. For example, in one embodiment, the elongated member 102 is made primarily of stainless steel while the notches 200 comprise regions of the elongated member 102 made of a different material, for example an elastic compound. The notches 200 thus represent discontinuities in the material of the wall of the elongated member 102, without necessarily changing the profile or thickness of the elongated member 102.

The notches 200 may be operable to assist in directing a change in shape of the elongated member 102 when a force is applied to the elongated member 102 through an actuator 112. In one such embodiment as described above, the application of tension to the actuator 112 applies a force to an attachment point at the distal tip 108, pulling the attachment point in a proximal direction. As notches 200 may serve to locally increase the flexibility of the elongated member 102, the elongated member 102 may change shape to, for example, bend preferentially in the direction of the notches 200 when tension is applied. Thus, in some embodiments, the notches 200 may be shaped and positioned around the elongated member 102 such that the elongated member 102 will adopt a certain specific curve or series of curves when tension is applied to the actuator 112.

Figure 3A:
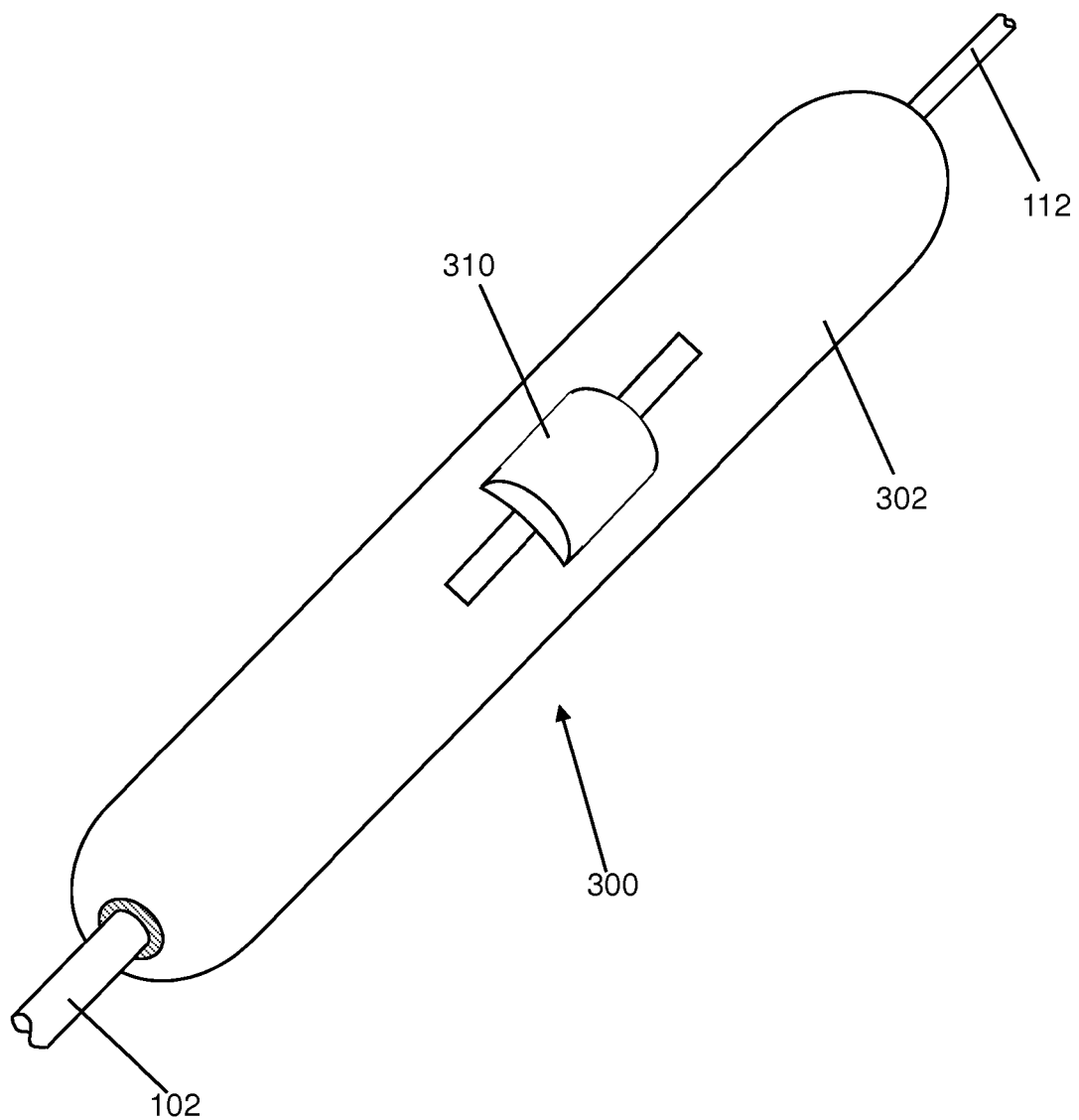
FIG. 3A, in a partial perspective view, illustrates an embodiment of a handle usable with the apparatus illustrated in FIGS. 1A to 2.
Figure 3C:
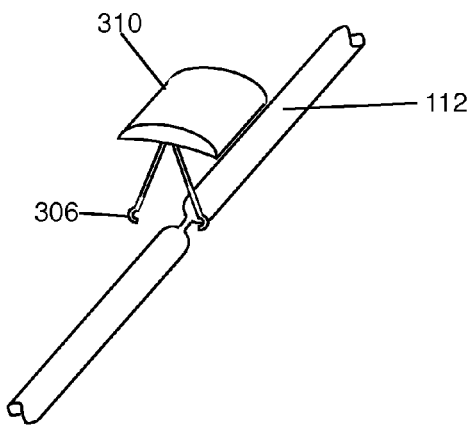
FIGS. 3C and 3D, in perspective views, illustrate an embodiment of a securing component usable with the handle shown in FIGS. 3A and 3B.
Figure 3D:
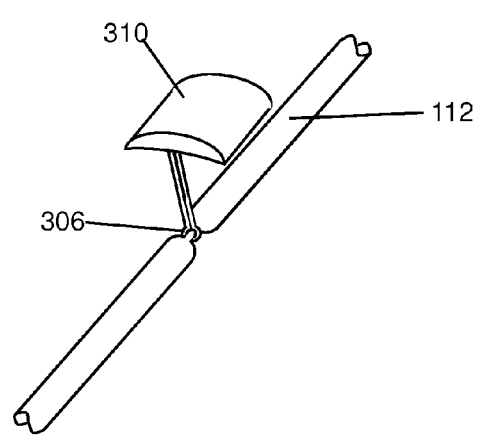
Figure 3B:
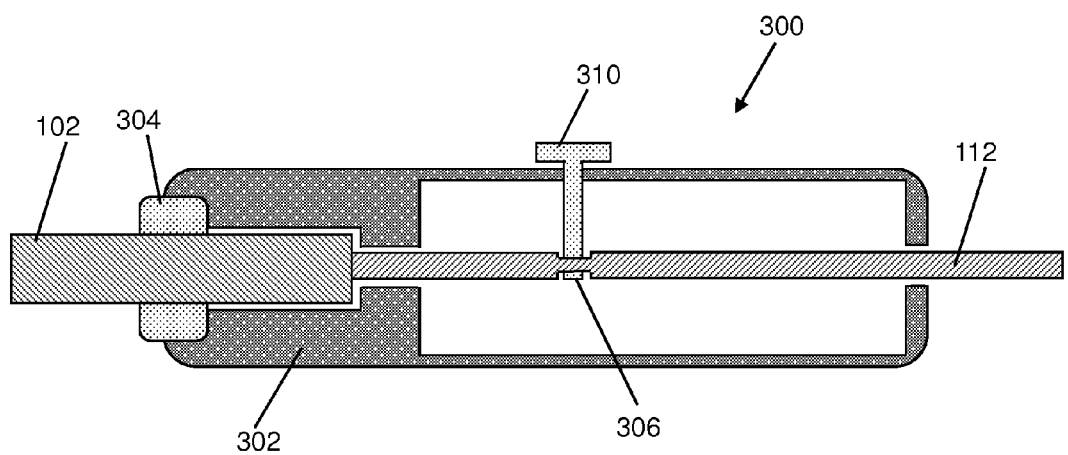
FIG. 3B, in a side cross-sectional view, illustrates the handle of FIG. 3A.

In some embodiments of the present invention, and referring now to FIG. 3A, apparatus 100 includes a handle 300 mechanically coupled to the proximal end region 106 of the elongated member 102. The handle 300 may be suitable for grasping and manipulating the apparatus 100, for example during insertion, positioning or guiding thereof, and may, in some embodiments, be operable to facilitate a change in shape of the elongated member 102. Referring to FIG. 3B, in some embodiments, the handle 300 comprises a housing 302, a first securing component 304 and a second securing component 306. The handle 300 may further comprise a means for connecting an energy source to one or more of the elongated member 102, the actuator 112 and any other electrical conductor operable to deliver energy to the electrode 110. For example, the handle 300 may comprise an electrical connector for connecting to an energy source. In such embodiments, the electrical connector may be coupled to handle the 300 via an electrical cable. Alternatively, as shown in FIG. 3B, the actuator 112 may extend from a proximal end of the handle 300 and may be operable to be electrically coupled to an energy source.

The first securing component 304 may be operable to secure the handle 300 to the elongated member 102, while the second securing component 306 is operable to secure the handle to the actuator 112. In the embodiment shown in FIGS. 3B to 3D, the second securing component 306 comprises a clamping apparatus operable to securely engage the actuator 112. Actuation of the handle 300 via, for example, a button 310, may effect a change in the relative positions of the first securing component 304 and the second securing component 306, thus causing the elongated member 102 and/or actuator 112 to move with respect to one another. However, actuation of the handle 300 may be achieved using any means for displacing a wire or similar component, including but not limited to one or more of a button, a knob and a switch. Actuation of the handle 300 may involve the use of mechanical (including linear, rotational and other forces) and/or electrical energy and may be accomplished remotely. In some embodiments, the handle 300 includes a ratcheting mechanism to maintain tension in the actuator 112, for example by maintaining the position of one or more of the first securing component 304 and the second securing component 306 following actuation of the handle 300. In some embodiments, the handle 300 may be removable. For example, in one such embodiment, the first and second securing components 304 and 306 are each detachable from the elongated member 102 and the actuator 112, respectively. In such embodiments, the handle 300 may further be re-attachable after having been removed. Furthermore, in such embodiments, the handle 300 may additionally comprise one or more visual markers and/or one or more locks or other fastening mechanisms to aid in the positioning and attachment of the first securing component and the second securing component 306 respectively to the elongated member 102 and the actuator 112. Such markers and/or locks may be useful to orient the direction of bending of the elongated member 102 with respect to the handle 300, and to calibrate the actuator 112 to the amount of tension already present in the actuating mechanism. In embodiments comprising an actuator 112 that utilizes means other than tension to direct apparatus 100 in a desired direction, the handle 300 may be operable to manipulate the actuator to effect the desired change in direction.

In accordance with embodiments of the present invention, any portion of the elongated member 102, the actuator 112, the notches 200, the electrode 110 or the insulating material 114 may comprise one or more markers. Such markers may include visual markers, tactile markers, radiopaque markers, radiolucent markers, or any other markers used to aid in the visualization, localization, navigation, insertion, or detection of apparatus 100. Markers may be externally applied to a component, and may be of a variety of shapes and structures; they may be raised from the surface of a component or may conform to the surface of the component; and they may be internal to a component. In some embodiments, components may be manufactured in whole or in part from materials that provide a visual or tactile distinction, thus acting themselves as markers. For example, in one embodiment, the insulating material 114 is manufactured from a radiopaque insulating material or from a material comprising radiopaque fillers. In another embodiment, one or more of the elongated member 102, the distal tip 108, the electrode 110 and the actuator 112 are plated with a radiopaque material, such as platinum or tungsten. In yet another embodiment, a radiopaque marker, such as a band, is welded or otherwise attached to, for example, the distal tip 108 or the electrode 110.

In some embodiments, as mentioned hereinabove, any or all of the lumen 116, the actuator 112 and the notches 200 may not be present in the apparatus, in order, for example, to simplify the process of manufacturing the apparatus 100 and make it more cost-effective. In addition, in such embodiments, the apparatus 100 may have substantially similar mechanical properties when compared to a standard mechanical guide-wire.

In some embodiments of the present invention, the apparatus 100 further comprises one or more means for guiding the apparatus 100 within the body of the patient. For example, in one particular embodiment, the apparatus 100 further comprises an ultrasound transducer (not shown in the drawings) associated with the distal end region 104. The ultrasound transducer (not shown in the drawings) may be operable as an intra-vascular ultrasound (IVUS) device, which may assist in determining the position of the apparatus 100 within a blood vessel, for example. In such an embodiment, the ultrasound transducer (not shown in the drawings) may be electrically connected to an ultrasound generator, for example via one or both of the elongated member 102 and the actuator 112. In another specific embodiment, the apparatus 100 further comprises at least one optical fiber (not shown in the drawings) which may be optically coupled to an optical coherence reflectometry (OCR) system (not shown in the drawings), which may also assist in determining the position of the apparatus 100 within a blood vessel, for example. Another example of a suitable device or apparatus is described in application Ser. No. 12/926,292, which is incorporated herein by reference in its entirety.

Materials

In embodiments wherein the elongated member 102 takes the form or includes an electrically conductive core wire, as described hereinabove, it may be made of a biocompatible metal or metal alloy, for example, including, but not limited to, stainless steel or nitinol. The actuator 112 may be conductive, and may, in some embodiments, have a high tensile strength, thus being able to tolerate the application of sufficient force to cause a change in shape of the elongated member 102, when a force is applied to the actuator 112. An example of a material that is suitable for the actuator 112 is nitinol. The insulating material 114 may be composed from any material capable of providing electrical insulation, including, in some embodiments, Parylene or polytetrofluoroethylene (PTFE). The insulating material 114 may be applied to the elongated member 102 by a variety of methods including, but not limited to: being overlain onto the elongated member 102 and shrunk by the application of heat, being extruded over the elongated member 102, and being sprayed or painted onto the elongated member 102 in liquid form. Suitable materials for radiopaque markers or components include, but are not limited to, high-density metals such as platinum, iridium, gold, silver, tantalum, and tungsten or their alloys, or radiopaque polymeric compounds. Although the above materials are suggested as being suitable options for the manufacture of components of the present invention, the list is by no means meant to be limiting, and any other components with suitable properties may be used.

Method

In some embodiments, the apparatus 100 is usable to create a channel in a foreign material located the body of a patient (not shown in the drawings). This channel may be created, in some embodiments, at least partially by the delivery of energy using the electrode 110. More specifically, the electrode 110 is energized with a radiofrequency current and the electrode 110 is then used to deliver energy into the foreign material to create the channel. In some embodiments, the energy delivered in the foreign material is thermal energy.

Without being limited to a particular theory of operation, it is hypothesized that, in some embodiments, the proposed method is performed when the electrode 110, which is energized with a radiofrequency current, heats up to a predetermined temperature. For example, the predetermined temperature may be substantially larger than a melting temperature of the foreign material. Then, thermal energy is transferred from the electrode 110 to the foreign material to substantially melt the foreign material adjacent to the electrode 110, thereby creating a channel through the foreign material. In other embodiments, it is hypothesized that water may be absorbed by the foreign material, and radiofrequency energy that is thereafter delivered to the foreign material may cause vaporization of the water adjacent to the electrode 110, thereby creating a channel through the foreign material.

In some embodiments, heating of the electrode 110 is performed while the electrode 110 is positioned at a predetermined distance from the foreign material and from biological tissues adjacent to the foreign material. Positioning the electrode at a predetermined distance from the foreign material and from the biological tissues adjacent to the foreign material minimizes risks of injuring the biological tissues adjacent to the foreign material. For example, the predetermined distance is such that thermal energy transfer between the electrode 110 and either or both of the foreign material and biological tissues adjacent to the foreign material results in a non-damaging increase in temperature thereof. As mentioned hereinabove, the use of a radiofrequency current to heat the electrode 110 helps in minimizing this heat transfer, and therefore contributes to the practicality of the proposed method as the predetermined distance is then relatively small.

Minimizing injuries to tissues is of paramount importance when performing interventions in patients. Indeed, injuring a tissue typically creates stress and inflammatory responses that may cause irreversible damages to many tissues. In addition, many patients have a relatively sensitive hypothalamic-pituitary-adrenal axis (HPA axis) and local stresses to tissues can lead in these patients to systemic and psychiatric conditions and diseases. In some embodiments, the proposed method is performed in the heart of the patient. In these cases, these irreversible damages can lead to dysfunctions in the contractile and electrical conductivity properties of the cardiac tissue, which themselves can lead to life-threatening conditions.

It is hypothesized that providing the radiofrequency current to the electrode 110 within the body creates a layer of water vapor around the electrode 110, which reduces thermal transfer between the electrode 110 and adjacent structures that are sufficiently spaced apart therefrom. This helps in ensuring a relatively fast heating of the electrode 110 and reduce risks of damaging biological tissues as described hereinabove.

In such embodiments, the electrode 110 is then moved so as to be substantially adjacent to the foreign material. As the electrode has now attained a temperature substantially higher than the melting temperature of the foreign material, the electrode effectively melts the foreign material to create a channel therethrough.

However, in alternative embodiments of the invention, positioning of the electrode 110 substantially adjacent to the foreign material, for example to a first surface of the foreign material, is performed before energizing the electrode 110.

Generally speaking, the aforementioned specifics of the proposed method are typically part of a treatment procedure comprising the steps of: providing the apparatus 100, or any other suitable apparatus; inserting at least a portion of the apparatus 100 into the body of the patient, for example by introducing the distal end region into the body of the patient; positioning the electrode 110 substantially adjacent to the material first surface; energizing the electrode 110 with a radiofrequency current; and using the electrode 110 energized with the radiofrequency current to deliver energy into the foreign material to create the channel. Further embodiments may comprise additional steps of, for example, manipulating an actuator, or otherwise guiding the apparatus 100 through one or more of the body vasculature of the patient and the channel.

In accordance with embodiments of the treatment method aspects of the present invention, the apparatus 100 may be a component of a system including an energy source (not shown in the drawings) (such as, for example, the RFP-100 or RFP-200 Baylis Medical RF Puncture Generators, manufactured by Baylis Medical Company Inc., Montreal, Canada), and a grounding pad (not shown in the drawings) or any other return electrode, if operated in a monopolar mode.

Figure 4:
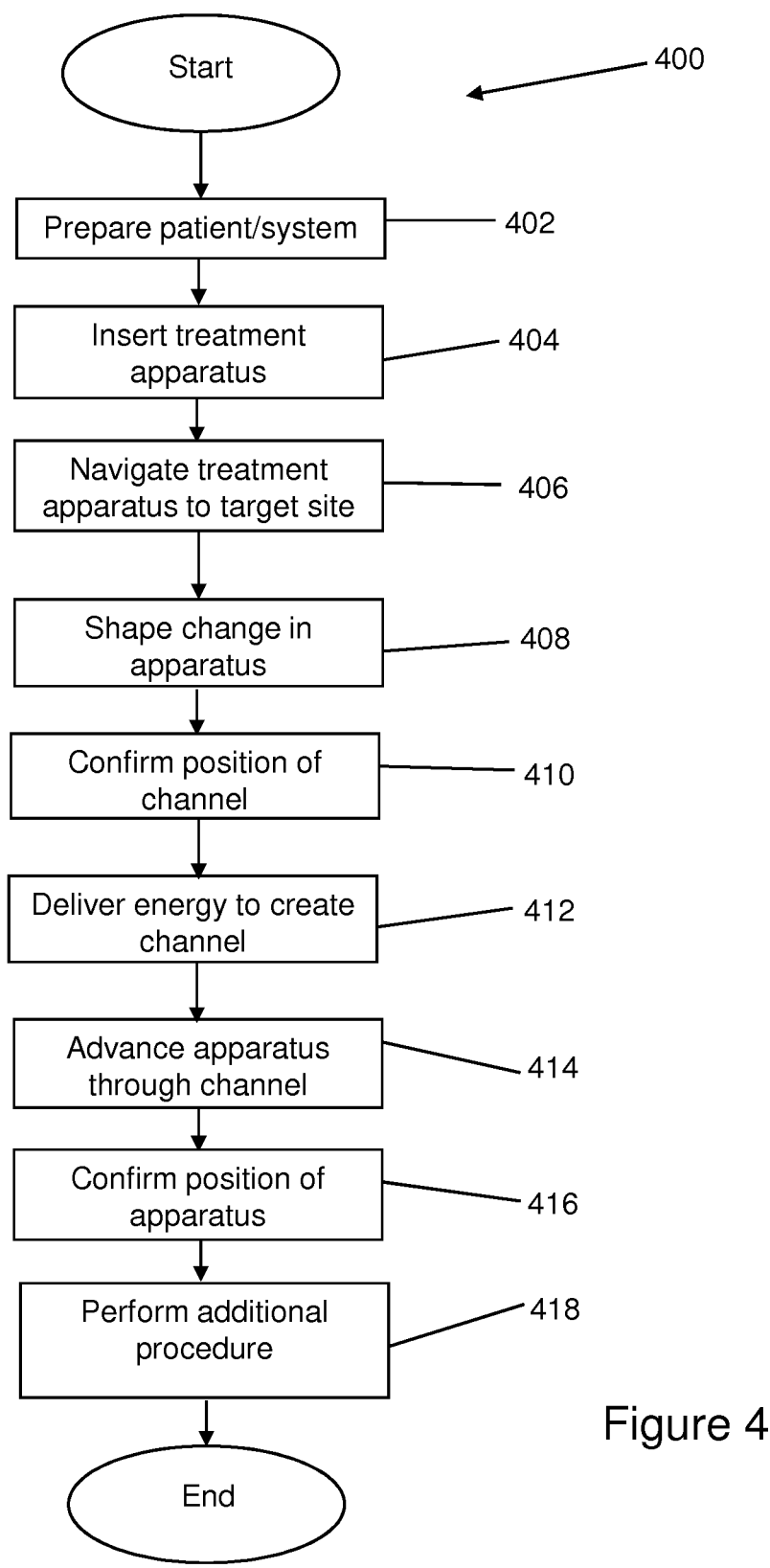
FIG. 4, in a flow chart, illustrates a method for creating a channel in a foreign material in accordance with an embodiment of the present invention.

FIG. 4 illustrates, in a flow-chart form, one embodiment of a method 400 in accordance with the present invention. This embodiment comprises: at step 402, preparing a patient and a system for treatment; at step 404, inserting a portion of the apparatus 100, into the body vasculature of the patient; at step 406, navigating the apparatus 100 through the body vasculature to a target site; at step 408, changing a of shape, or otherwise reorienting the apparatus 100 in order to position the electrode 110, or any other suitable electrode, adjacent at least a portion of the foreign material; at step 410, confirming or otherwise assessing the position of the electrode 110; at step 412, delivering energy via the apparatus 100 to create a channel in the foreign material; at step 414, advancing the apparatus 100, for example the distal end region 104 and the electrode 110, through the channel; at step 416, assessing the position of the electrode 110 or any other portion of the apparatus 100 after it has been advanced through the channel; and, at step 418, performing an additional procedure at or around the target site. The reader skilled in the art will readily appreciate that the patient may be a human or an animal and that one or more of these steps may not necessarily be performed in a given procedure or that one or more of these steps may be performed in a different order, as will be further clarified hereinbelow.

In step 402, preparing a patient for treatment may include, but is not limited to one or more of: visualizing one or more treatment sites within the body of the patient using fluoroscopy, x-ray, contrast media, labeled markers such as radioactive compounds or solutions, using endoscopy procedures, using ultrasound, using Doppler imaging, or any other visualization method; characterizing the vascular system of the patient by measuring blood or serum levels of various compounds; measuring vascular pressure; and undertaking any other measuring or monitoring technique that may provide information that may be useful during any other step of the method. In step 402, preparing a system for treatment may include, but is not limited to one or more of: connecting a treatment apparatus, for example the apparatus 100 as described above, to an energy source; connecting a grounding pad or other return electrode to the energy source; placing the grounding pad or return electrode on the body of the patient; passing the actuator 112 through the elongated member 102 (in some embodiments, the actuator 112 may be permanently threaded through the elongated member 102, thus obviating this step), if the apparatus 100 comprises the actuator 112; securing the handle 300 to the actuator 112 and the elongated member 102 (in some embodiments, the handle 300 may be permanently connected to the elongated member 102 and the actuator 112, thus obviating this step); and attaching one or more additional components to the apparatus 100. As mentioned above, one or more of these steps may not be performed in a particular procedure, depending on the apparatus 100 being used and the specific procedure being performed.

The step 404 of inserting the apparatus 100 into the body vasculature of the patient may comprise percutaneously inserting the apparatus 100 into a blood vessel of the body vasculature through which the apparatus may be navigated to the target site. For example, in some embodiments, the apparatus 100 may be inserted into a femoral artery or vein or a subclavian artery or vein. The apparatus may be inserted directly into the blood vessel or may be inserted through a guiding catheter or sheath.

The step 406 of navigating the apparatus 100 through the body vasculature to a target site may involve advancing the apparatus 100 through the body vasculature to the target site. In some specific embodiments, in which the apparatus is inserted through a guiding sheath or catheter, the sheath or catheter may initially be navigated to the target site, for example by initially inserting a guidewire to the target site and then tracking the sheath/catheter over the guidewire. Once the sheath/catheter is in place, the guidewire may be removed and the apparatus 100 may be inserted through the sheath/catheter. Step 406 may additionally involve any of a variety of visualization techniques, including those techniques mentioned above for visualizing one or more treatment sites within the body of the patient. In one embodiment, the apparatus 100 may be furnished with one or more radiopaque markers, which may aid in the visualization of the apparatus 100.

The step 408 of affecting a change of shape in the apparatus 100 may be required, for example if the step of navigating the apparatus 100 does not position the apparatus 100 sufficiently precisely. This step is, in some embodiments, accomplished by effecting a change of shape in the distal end region 104 of the elongated member 102, as described hereinabove. In some embodiments, it may be desirable to approach the foreign material substantially perpendicularly, for example at an angle of about 80 degrees to about 100 degrees, and step 408 is usable to control this angle.

The step 410 of confirming a position of the apparatus 100 may involve visualizing the position of one or more portions of the apparatus 100 within the body of the patient. For example, radiopaque markers included in the apparatus 100 may be visualized using fluoroscopy. Alternatively, or in addition, radiopaque contrast may be injected, for example through the guiding sheath/catheter, in order to confirm the position of the apparatus 100. Furthermore, in some embodiments, the apparatus 100 may include a pressure sensor (not shown in the drawings) operatively coupled to the distal end region of the apparatus for measuring a pressure at or around the distal end of the apparatus. In such embodiments, blood pressure may be reassured in order to confirm the position of the apparatus.

The step 412 of delivering energy may include an optional step of measuring, assessing or sensing the composition of the foreign material to be penetrated. For example, in one embodiment, the apparatus 100 may be used as part of an impedance monitor to determine the impedance of the material to be penetrated. The impedance value thus measured may then be compared to known impedance values of various materials in order to determine the composition of the material to be penetrated. Then, energizing the electrode 110 is performed, in some embodiments, at least in part, in a manner depending on the composition of the foreign material. For example, the electrode 110 may be energized at various power levels, depending on the nature of the foreign material. Alternatively, a change in impedance may indicate that the material in contact with the apparatus has changed. For example, a lower impedance may indicate that the apparatus is in contact with a metallic or otherwise conductive portion of a stent or scaffold, as opposed to the graft material associated with the stent/scaffold. In such a situation, a user may reposition the apparatus until a suitable impedance measurement is recorded indicating that the apparatus is substantially adjacent to the foreign material through which the channel is to be created.

Alternatively, tactile feedback may be used to assist in determining the material in contact with the apparatus. For example, a user may use tactile feedback to determine whether the apparatus is in contact with metallic material of a stent/scaffold or more flexible graft material, through which a channel may be created. Alternatively, or in addition, imaging techniques (for example OCR and/or IVUS) may be used to determine the composition of material in contact with the apparatus 100. As described hereinabove, the composition of the material to be penetrated may determine the initial parameters of energy delivery.

The step 412 of delivering energy via the apparatus 100 to create a channel in the foreign material comprises, in one embodiment, delivering electromagnetic energy (for example electric energy in the radiofrequency (RF) range) to the electrode 110. In one specific embodiment, the RF current provided may have a frequency in the range of from about 300 kHz to about 1 MHz, and more specifically, in very specific embodiments of the invention, of from about 460 kHz to about 500 kHz, and may be delivered with a power of at least about 5 W at a voltage of at least about 75 Volts (peak-to-peak).

In some embodiments, one or more parameters may be measured substantially while energy is being delivered and/or the device is being advanced. For example, impedance may be measured substantially continuously or at predetermined intervals during energy delivery and/or advancement of the apparatus and a change in impedance may lead to a change in energy delivery. In one particular example, a drop in impedance may indicate that the apparatus is contacting a metallic portion of a stent/scaffold and energy delivery may be stopped so that the device may be repositioned. The change in energy delivery may be automatic or may be manually performed by the user.

In some embodiments of the invention, the energy may be delivered for a predetermined amount of time before stopping the delivery of the energy. In other embodiments, the intended user may decide, during the course of the procedure, on the amount of time during which energy should be delivered. The intended user's decision may depend, for example, on one or more of tactile feedback, impedance measurements, pressure measurements, predetermined information regarding the material being penetrated (e.g. the thickness of the material) or the preferences of the intended user. In one example, if a user feels that the device has penetrated through the foreign material he may stop delivering energy. In some embodiments, the amount of time during which energy is delivered is from about 0.1 seconds to about 5 seconds. In a more specific embodiment of the invention, the amount of time during which energy is delivered is from about 1 second to about 2 seconds. During these periods of time, the energy may be delivered continuously or as a pulsed waveform.

The step 414 of advancing the apparatus through the channel may comprise applying a longitudinal force to the proximal end region 106 of the apparatus 100 in order to advance the distal end region 104 of the apparatus 100 through the channel. Alternatively, mechanical or magnetic means for advancing the apparatus may be used. In some embodiments, step 414 occurs at least partially concurrently with step 412, such that the apparatus is advanced while energy is being delivered.

Following step 414, the position of the apparatus 100, after passing through the channel, may be confirmed at step 416. Step 416 may be performed in substantially the same manner as step 410, described hereinabove.

The step 418 of performing another treatment procedure may involve, in some embodiments, one or more of: introducing a balloon catheter, a dilator or other means for dilation of the channel, to the target site, for example overtop of or through the apparatus 100; introducing a stent or other supporting structure to the target site, for example overtop of or through the apparatus 100; delivering a pharmaceutical compound to the target site; delivering energy to create a lesion or coagulate tissue or fluid in the vicinity of the target site; introducing embolic coils; placing an IVUS or OCR probe for visualization; or adding or removing any other material to or from the site. In addition, this step may further comprise removal and possible re-attachment of the handle 300 of the apparatus 100, in order to allow for the introduction of another device to the treatment site. As mentioned hereinabove, in alternative embodiments of the invention, the electrode 110 is energized after having been positioned adjacent to the foreign material.

Embodiments of the treatment procedure described above may be particularly useful to create a channel through material of a stent graft occluding one or more vessels of a patient's body. Several examples of such applications are noted hereinbelow. While these examples have been described in specific detail, one of skill in the art will appreciate that embodiments of the present invention may be utilized in various other procedures and applications.

EXAMPLES

Example 1

Figure 5A:
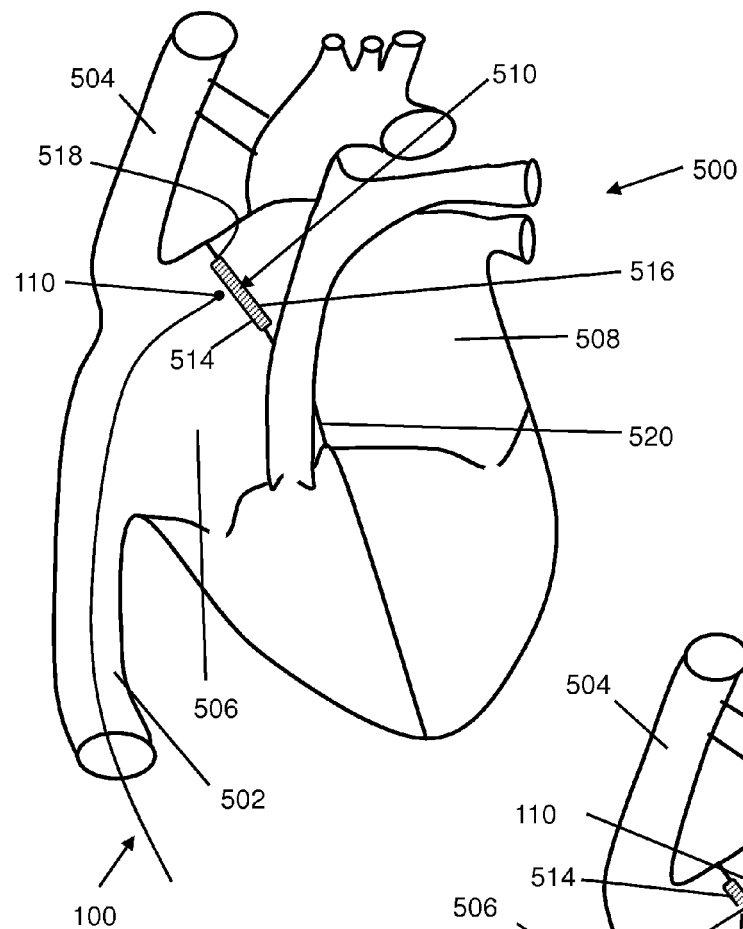
FIGS. 5A and 5B, in schematic views, illustrate a method for creating a channel in a septal patch extending across an aperture formed in the heart of a patient in accordance with an embodiment of the present invention.
Figure 5B:
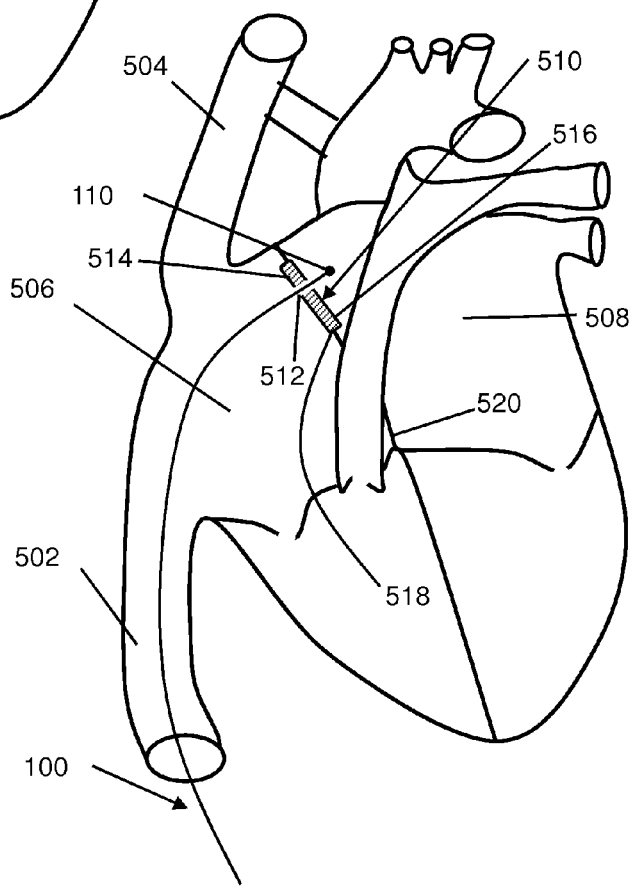

In a first example, an embodiment of a proposed method is used to create a channel 512, seen in FIG. 5B, within a septal patch 510 made of foreign material, the septal patch 510 defining a material first surface 514 and a substantially opposed material second surface 516. The channel 512 extends between the material first and second surfaces 514 and 516. The septal patch 510 extends across an aperture 518 defined by the septum 520 of the heart 500 of the patient, for example an atrial septum or a ventricular septum. For example, the septal patch 510 covers the aperture and extends in a plane outside of the septum 520. In other examples, the septal patch 510 extends inside the aperture 518. Some of these procedures may involve patients that have had a septal defect repaired with the septal patch 510. In some cases, such patients may suffer from one or more conditions which require access to the left side of the heart for treatment to be performed. In such situations, access to the left side of the heart may be gained by creating the channel 512 in the septal patch 510. In such embodiments, the septal patch 510 may be made of a foreign material selected from the group consisting of polyethylene terephthalate (PET, for example Dacron®), cotton, a polyester material and fabrics thereof.

With reference to FIG. 5A, the apparatus 100 is inserted through the inferior vena cava 502 into the right atrium 506 of the heart 500. In alternative embodiments, access to the right atrium may be achieved via the superior vena cava 504 as described, for example, in U.S. patent application Ser. No. 11/265,304 (Filed on Nov. 3, 2005), now U.S. Pat. No. 7,947, 040, which is incorporated herein by reference in its entirety.

FIG. 5A shows the apparatus 100 positioned in the right atrium 506 with the electrode 110 located substantially adjacent the material first surface 514. FIG. 5B shows the apparatus 100 positioned in the left atrium 508 after being advanced through the channel 512. In this particular embodiment, radiofrequency energy may be delivered, for example, at about 5 W for a period of less than about 5 seconds.

In a further example application, an embodiment of a method according to the present invention may be useful, for example, to create a channel within a graft composed of foreign material. In some embodiments, the graft is associated with a substantially tubular supporting structure, for example a stent, located within an elongated vessel of the body of the patient. In some such embodiments, the method is performed in order to restore blood flow to a branch of the elongated vessel being occluded by the graft material, thus substantially preventing fluid communication between the branch and the elongated vessel, by creating a channel through the material.

With reference now to FIGS. 6A, 6B, 7A and 7B, methods for in-situ creation of a channel through a stent-graft are illustrated. In the illustrated embodiments, a stent-graft 606, composed of a foreign material, has been placed to cover an aneurysm 604 in an abdominal aorta 600. As shown in these figures, stent-graft 606 occludes the renal arteries ostia 605.

This positioning of the stent-graft 606 is typically necessitated by an inadequate, i.e. too short, proximal neck of the abdominal aorta 600. One of the greatest challenges of stent-grafting an abdominal aortic aneurysms 604 is to obtain a long proximal attachment site to ensure a good seal without occluding the renal or supra-aortic vessels. If a long proximal site is unavailable, the ostia of the renal and/or supra-aortic vessels may become occluded by the stent-graft 606. The present invention provides a method for creating a transluminal in-situ channel in order to restore blood flow to any vessels that do become occluded during the course of such a procedure.

Example 2

With reference first to FIGS. 6A and 6B, an antegrade approach to in-situ channel creation is provided. In this approach, the distal end region 104 is introduced into the body of the patient through the body vasculature inside the thoracic cavity, or in other words from a position superior to the diaphragm of the patient, and advanced towards the abdominal aorta 600 in which the electrode 110 is then positioned. FIG. 6A shows the electrode 110 of the apparatus 100 positioned in the abdominal aorta 600 substantially opposite the renal artery ostium 605, which is occluded by the stent-graft 606. At this point, energy may be delivered from an energy source through the electrode 110 in order to create a channel 608, as seen in FIG. 6B, in or through the stent-graft 606. FIG. 6B shows the electrode 110 after it has been advanced through the channel 608 into the renal artery 602. Creation of the channel allows for fluid communication and restoration of blood flow between the abdominal aorta 600 and the renal artery 602. At this point, as described above with respect to FIG. 4, the channel 608 may be dilated using one or more of a dilator and a balloon (for example a cutting balloon) and a stent may be placed across the channel 608 to maintain the patency of the renal artery 602.

Figure 7A:
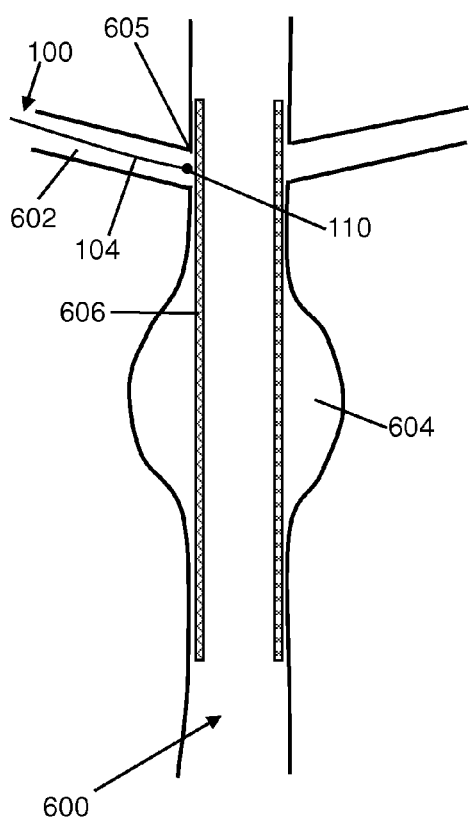
FIGS. 7A and 7B, in schematic views, illustrate a method for creating a channel in a stent graft extending across an ostium of a renal artery of a patient in accordance with an alternative embodiment of the present invention.
Figure 7B:
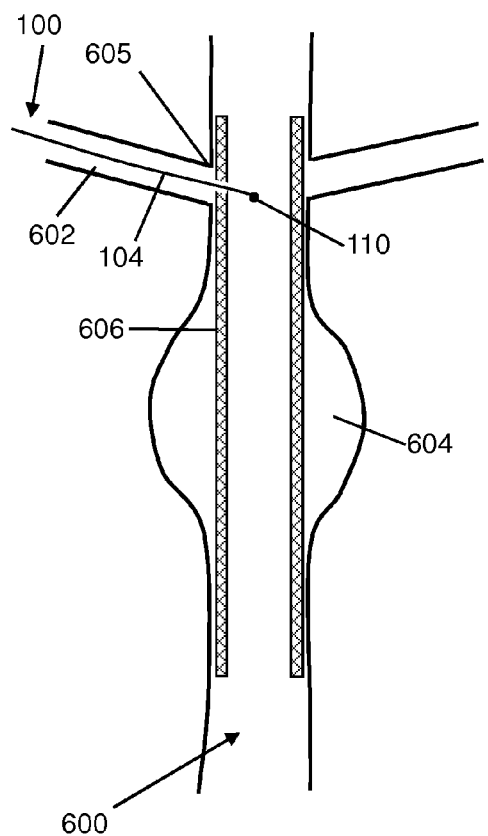

With reference now to FIGS. 7A and 7B, a retrograde approach is illustrated. In this approach, introducing the distal end region 104 into the body of the patient includes introducing the distal end region into the body vasculature and through the renal artery 602 towards the abdominal aorta 600.

In such an embodiment, positioning the electrode 110 substantially adjacent to a material first surface then includes positioning the electrode 110 substantially adjacent to the renal artery ostium 605 outside of the abdominal aorta 600.

With reference first to FIG. 7A, the electrode 110 of the apparatus 100 is positioned in the renal artery 602 at the renal artery ostium 605, which is occluded by the stent-graft 606. At this point, energy may be delivered from an energy source through the electrode 110 in order to create a channel 608 in or through the stent-graft 606. FIG. 7B shows the electrode 110 after it has been advanced through the channel 608 into the abdominal aorta 600. As mentioned hereinabove, creation of the channel 608 may allow for fluid communication and the restoration of blood flow between the abdominal aorta 600 and the renal artery 602. At this point, as described above with respect to FIG. 4, the channel 608 may be dilated using one or more of a dilator and a balloon (for example a cutting balloon) and a stent may be placed across the channel to maintain the potency of the renal artery. It should be noted that in the embodiment of FIGS. 7A and 7B, step 404 of the method comprises obtaining access to renal artery 602, for example during a surgical procedure or via a deep puncture.

It should be noted that, although this example has been described in conjunction with treatment of an abdominal aortic aneurysm, a similar method is also contemplated for treating a thoracic aortic aneurysm, whereby a subclavian artery, for example, may become occluded by a stent-graft. Such a condition may be more easily treated using a retrograde approach, by inserting an apparatus through the subclavian artery towards the aorta. In addition, vessels other than the renal arteries 602 may be occluded by an abdominal aortic stent-graft, for example the mesenteric arteries (not shown in the drawings). Alternatively, similar embodiments of the method may be practiced in other situations whereby a vessel ostium (or any portion of an elongated vessel, tube and/or duct) in a patient's body is occluded by a foreign material.

Example 3

With reference now to FIGS. 8A-8D, alternate methods for in-situ creation of a channel through a stent-graft are illustrated. In the illustrated embodiments, a stent-graft 806, composed of a foreign material, has been placed to cover an aneurysm 804 in a section of the descending aorta, more specifically, within the thoracic aorta 800. As shown in these figures, the stent-graft 806 occludes the opening or ostium 805 of the Left Subclavian Artery (LSA) 802.

In the illustrated example, the positioning of the stent-graft 806 at the LSA ostium 805 is necessitated by the proximity of the LSA ostium 805 to the site of the aneurysm 804. A challenge is generally presented when an aneurysm 804 occurs within a vessel near an ostium of a side branch vessel, such as the LSA 802. It may become difficult to place the stent-graft 806 within the vessel to ensure protection of the aneurysm 804 while maintaining patency of the side branch ostium. In one such example, the aneurysm 804 and the LSA ostium 805 are located substantially adjacent each other. "Adjacent" may be taken to mean next to, in proximity to, near to, or in the vicinity of. In one example the aneurysm 804 and the LSA ostium 805 are located opposite to one another along the coronal and/or saggital planes. In other words, the aneurysm 804 and the LSA ostium 805 are radially opposed to one another. In a further example, the aneurysm 804 and the ostium 805 may be positioned axially adjacent to one another. In other words, the aneurysm 804 and the LSA ostium 805 may be positioned substantially collinearly with respect to each other. Thus, the proximity of the aneurysm 804 to the LSA ostium may necessitate the positioning of the stent-graft 806 such that it covers the aneurysm 804 but also occludes the LSA ostium. This positioning of the stent-graft 806 is typically necessitated by an inadequate, i.e. too short, proximal neck of the thoracic aorta 800. One of the greatest challenges of stent-grafting a thoracic aortic anerurysm 804 is to obtain a long proximal attachment site to ensure a good seal without occluding any of the side branch vessels such as the Left Subclavian Artery (LSA) 802, the Right Subclavian Artery (RSA) 808', Left Common Carotid Artery (LCCA) 810 or Right Common Carotid Artery (RCCA) 812. If a long proximal site is unavailable, then an ostium of a side branch vessel may become occluded by the stent-graft 806. For the specific case shown in FIGS. 8A-8D, to treat a thoracic aortic aneurysm, the LSA ostium may become occluded by the stent-graft 806. This illustrated embodiment of the present invention provides a method for creating a transluminal in-situ channel in order to restore blood flow to any vessels that do become occluded during the course of such a procedure.

With reference first to FIGS. 8B, and 8C, a retrograde approach to in-situ channel creation is illustrated. In this approach, introducing the distal end region 104 of apparatus 100 into the body of the patient includes introducing the distal end region 104 into the body vasculature and through the left subclavian artery (LSA) 802 towards the thoracic aorta 800. In one specific example, a guide sheath 900 is introduced into the body of the patient through the body vasculature and advanced into the LSA via the left brachial artery. The sheath 900 is advanced till a distal end of the sheath 900 is located about 5 cm from the stent-graft 806. The apparatus 100 according to an embodiment of the present invention, along with a guide catheter (not shown), is then be inserted through the guide sheath 900. The distal end region 104 of apparatus 100 is then advanced towards the LSA such that the electrode 110 is positioned adjacent the stent-graft 806 that is occluding the LSA ostium 805. In such an embodiment, positioning the electrode 110 substantially adjacent to a material first surface includes positioning the electrode 110 substantially adjacent to the LSA ostium 805 outside of the thoracic aorta 800. In some embodiments, a curved guide catheter or a centering mechanism may be used to direct the apparatus 100 towards the center of the LSA to position electrode 110 at the desired target location. In one example, a balloon catheter may be used to centre the apparatus 100 within the vessel.

When creating a channel through a stent-graft such as stent-graft 806, a strut 807 of the stent forming the stent-graft 806 may obstruct advancement of apparatus 100 through the stent-graft 806. In some embodiments of the present invention, a guide catheter is used to direct the apparatus 100 around the strut 807, as follows: The guide catheter and apparatus 100 may be aligned with the stent such that they are positioned against the strut 807. Gentle buckling of the catheter/apparatus assembly may be used to confirm that the catheter/apparatus assembly is positioned against the stent. The guide catheter may be incrementally adjusted around the strut 807 such that it is no-longer blocked by the strut 807. In some embodiments, a Right Anterior Oblique (RAO) view under fluoroscopic imaging may be used to guide the catheter and the apparatus 100 to the appropriate position.

Once the electrode is positioned appropriately, energy is delivered through the electrode 110 to puncture through the graft to create a channel 808 there-through. In some embodiments, the energy may be applied at a voltage of about 400 Vrms, with a duty cycle of 25 ms ON/975 ms OFF. In one particular example, energy is applied using the Baylis RFP-200 Generator at a high power setting for 2 seconds to puncture the graft/fabric of the stent-graft. In another example, it may be sufficient to deliver energy twice at durations of 1 second. The apparatus 100 may then be advanced into the stent-graft 806 under fluoroscopic guidance. In some embodiments, the energy may be delivered with the power being in the range of between about 30 Watts to about a 100 Watts; and the voltage may be in the range of between about 300 Vrms to about 500 Vrms. In some embodiments the energy may be applied for duration of at least 25 ms. Furthermore, in some embodiment the ON period of the duty cycle may range from between about 25 ms to about 1000 ms.

Figure 8A:
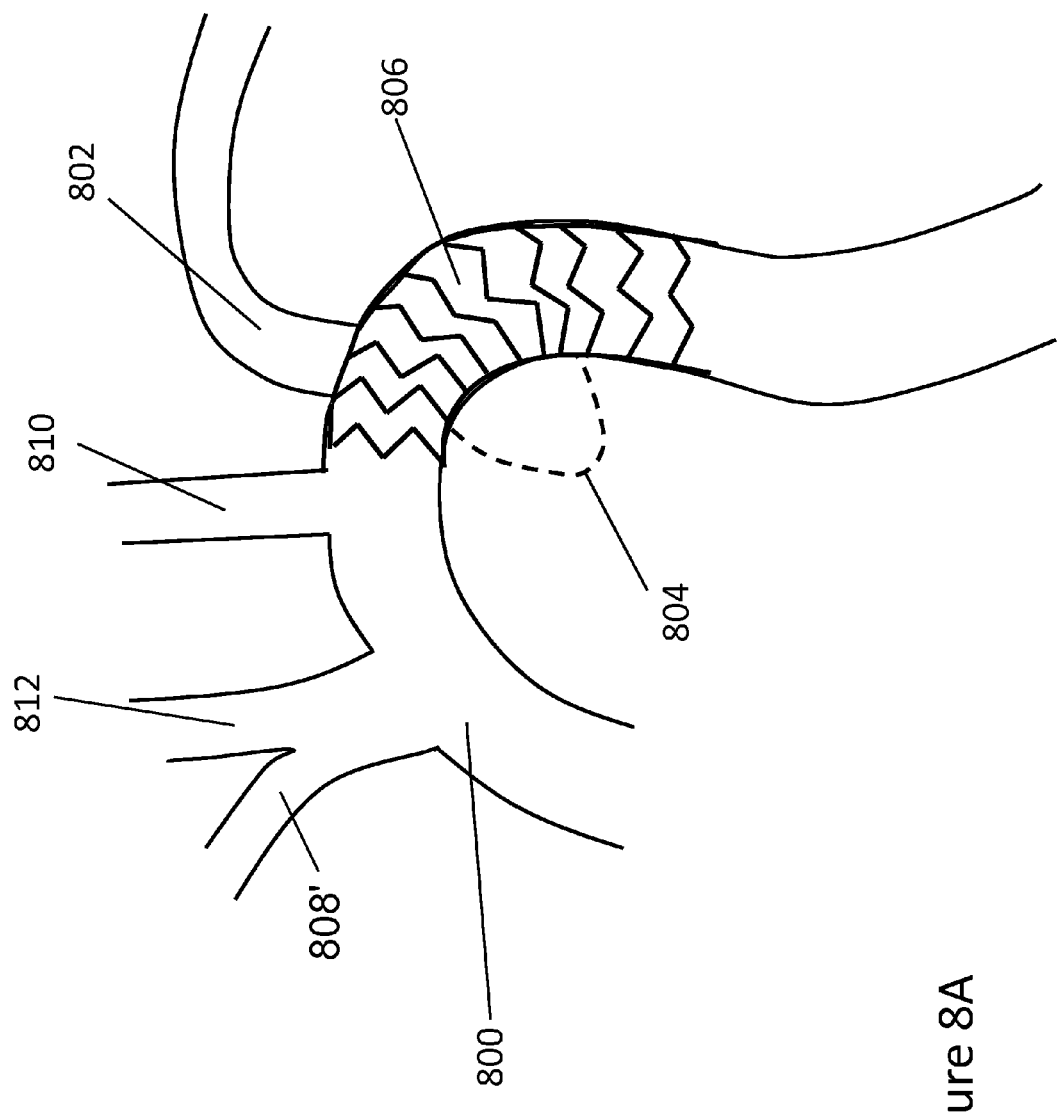
Figure 8D:
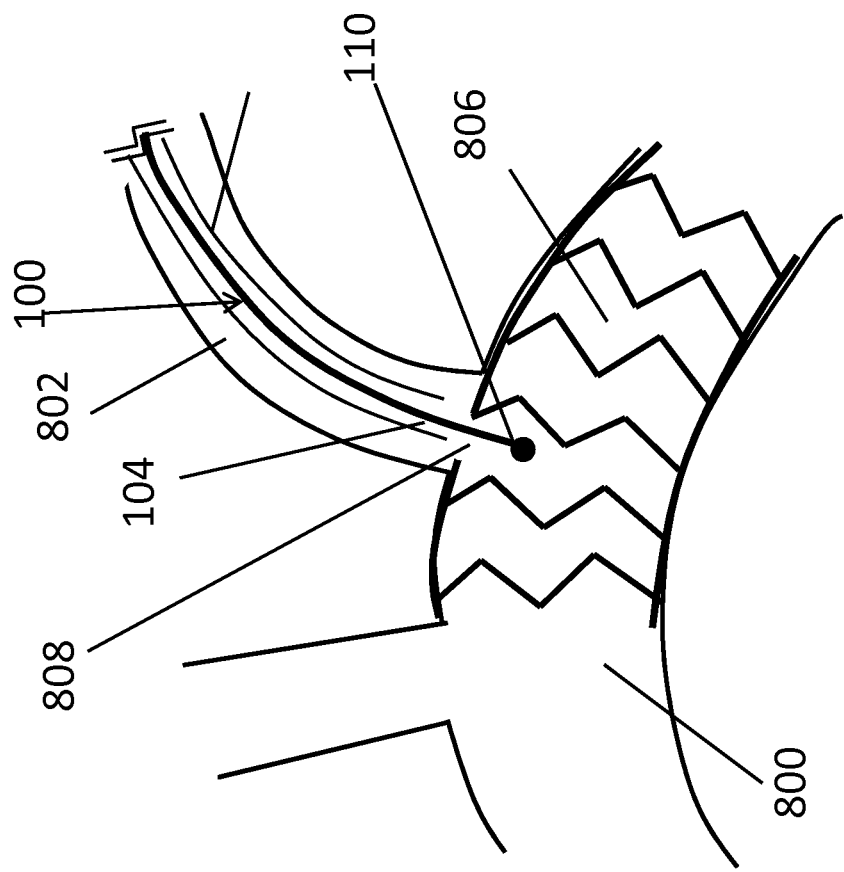
FIG. 8D, in schematic view illustrates a method for creating a channel in a stent graft extending across an ostium of a left Subclavian Artery (LSA) of a patient in accordance with an alternative embodiment of the present invention.

FIG. 8D shows the electrode 110 after it has been advanced through the channel 808 into the thoracic aorta 800. As mentioned hereinabove, creation of the channel 808 may allow for fluid communication and the restoration of blood flow between the thoracic aorta 800 and the LSA 802. At this point, as described above with respect to FIG. 4, the channel 808 may be dilated using one or more of a dilator and a balloon (for example a cutting balloon) and a stent may be placed across the channel to maintain the patency of the LSA. It should be noted that in the embodiment of FIGS. 8B and 8C, step 404 of the method comprises obtaining access to LSA 802, for example during a surgical procedure or via a deep puncture.

An additional challenge that may be faced when creating a channel through a stent-graft using radiofrequency energy is contact of the energized electrode with a strut, for example strut 807, of the stent-graft 806. Embodiments of the present invention provide a method for indicating a metal contact error if the electrode 110 of the apparatus 100 is in contact with the strut 807. In accordance with such embodiments, the energy delivery system prevents delivery of energy when the electrode 110 is positioned adjacent to or in contact with the metallic strut 807 but allows the apparatus 100 to delivery energy near the electrically conductive strut 807 of the stent-graft 806. This allows the physician to continue to deliver energy from the electrode 110 and steer the electrode 110 away from the strut 807. Thus, the orientation or position of the electrode 110 may be re-adjusted by moving it around or away from the metal strut 807, while power is being delivered. This allows the user to deliver energy from electrode 110 while it is positioned close to the metallic strut 807, allowing electrode 110 to cut through the stent-graft 806, but generating a "metal detect" error if the electrode 110 is in contact with the metallic strut 807 or close enough to produce undesired arcing.

With reference first to FIGS. 9A and 9B, an antegrade approach to in-situ channel creation is provided. In this approach, the distal end region 104 is introduced into the body of the patient through the body vasculature and advanced towards the thoracic aorta 800 in which the electrode 110 is then positioned. In one specific example, femoral access is used to guide the distal end region 104 of the apparatus 100 into the lumen of the stent-graft 806 that is positioned within the thoracic aorta. FIG. 9A shows the electrode 110 of the apparatus 100 positioned in the thoracic aorta 800 substantially opposite the left subclavian artery (LSA) ostium 805, which is occluded by the stent-graft 806. At this point, energy may be delivered from an energy source through the electrode 110 in order to create a channel 808, as seen in FIG. 9B, in or through the stent-graft 806. FIG. 9B shows the electrode 110 after it has been advanced through the channel 808 into the left subclavian artery (LSA) 802. Creation of the channel allows for fluid communication and restoration of blood flow between the thoracic aorta 800 and the LSA 802. At this point, as described above with respect to FIG. 4, the channel 808 may be dilated using one or more of a dilator and a balloon (for example a cutting balloon) and a stent may be placed across the channel 808 to maintain the patency of the LSA 802.

Figure 10:
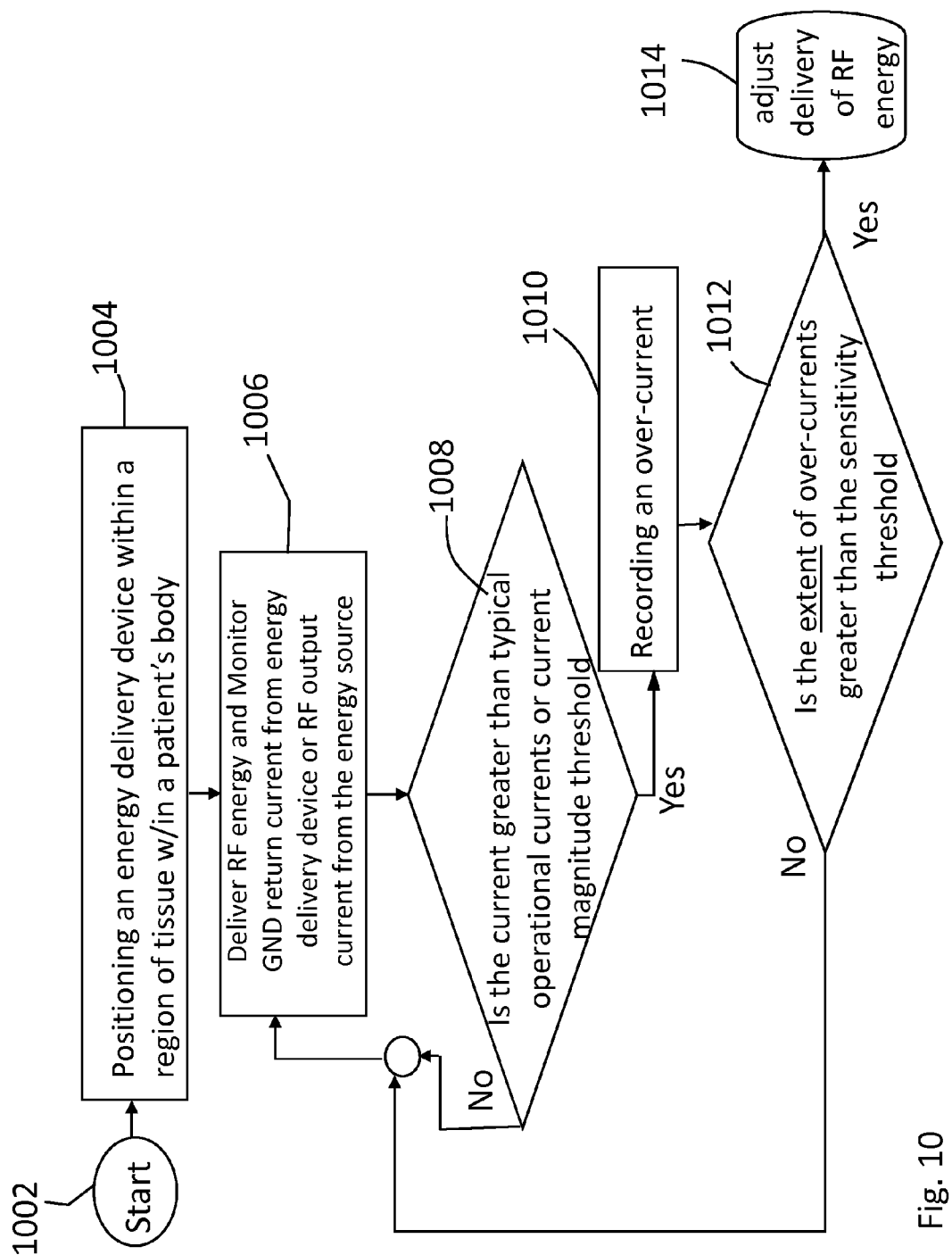
FIG. 10 is a flow chart showing steps of a method in accordance with an embodiment of the present invention.

FIG. 10 is a flow chart illustrating an example of such a method. As shown by step 1004, an energy delivery device such as apparatus 100 may be positioned within a region of tissue at a target location within a patient's body. At step 1006, an RF power source may be used to supply RF energy to the apparatus 100. An energy delivery parameter, for example the current output from the ground return pathway of the apparatus 100, is monitored. The measured values of the current are compared to a predetermined current range or magnitude threshold.

At step 1008, the measured current is analyzed to determine if it is greater than the predetermined threshold or range. If the current has peak currents that exceed the current magnitude threshold or normal operational currents, at step 1010 an excess current or over-current is recorded. If the monitored current is within the range of normal operational currents (below the predetermined current threshold), then the delivery of energy through the energy delivery device will not be interrupted and energy delivery can continue at step 906 and the current can continue to be monitored. At step 1012, a determination is made to assess whether or not the extent of over-currents recorded within a time period is greater than a predetermined sensitivity threshold and, if it is, then the energy delivery may be adjusted at step 1014. In one example, adjustment of the energy delivery comprises stopping the delivery of energy. In some embodiments, the extent of over-currents recorded may be determined in terms of the sum or magnitude of the over-currents recorded. In other embodiments, the extent of over-currents recorded may be determined in terms of the number or quantity of over-currents recorded. If the extent of over-currents is below the sensitivity threshold, then at step 1006 the energy delivery is continued while monitoring the current. Such a method as described above can thereby be utilized to prevent delivery of energy to the electrode when it would be detrimental to the patient to do so, for example when the electrode is positioned too close to a strut of the stent graft. Further details regarding the generation of a "metal detect" error as described hereinabove are found in U.S. provisional application No. 61/448,578, previously incorporated herein by reference.

A method for transluminal in-situ channel formation, for example as described herein, allows for more accurate placement of the channel, less reliance on preoperative imaging, increased availability and decreased cost of a "universal", non-customized graft, and eventually, more accessibility for a greater number of patients to the advantages of endovascular repair. As well, the technique could be used as a 'salvage' procedure when inadvertent coverage of side branches occurs. Most importantly, it would allow more accurate placement of the channels with the stent-graft in place in the aorta, rather than based on preoperative radiographic imaging.

The methods of the present invention provide a surprising and unexpected result in that energy, for example radiofrequency electrical energy is usable to create a channel in foreign material within the body of the patient, including, for example, synthetic material substantially not composed of cellular-based biological tissue (although it may, in some embodiments, be covered with live cells if, for example, it has been implanted in the body for a sufficient amount of time). In addition, embodiments of the present invention may minimize the risk of accidental puncture or perforation of a blood vessel or other bodily structure. Furthermore, embodiments of the present invention provide for the creation of a channel without requiring a mechanical tear of the foreign material. The methods of the present invention may also be useful in other applications, including, in general, wherever foreign material in a patient's body should be penetrated.

In accordance with one broad aspect, embodiments of the present invention provide a method for creating a channel through a foreign material located in a body of a patient, said foreign material defining a material first surface and a substantially opposed material second surface, said channel extending through said foreign material between said material first and second surfaces, said method using an apparatus including an electrode, said method comprising: positioning said electrode substantially adjacent to said material first surface; energizing said electrode with a radiofrequency current; and using said electrode energized with said radiofrequency current to deliver energy into said foreign material to create said channel; wherein said body includes a heart defining a septum, said septum comprising an aperture extending there-through and wherein said foreign material extends across the aperture to cover the aperture.

In accordance with another broad aspect, some embodiments of the present invention provide a method of gaining access into a left side of a heart, the heart having a septum defining an aperture, wherein foreign material extends across the aperture, said method using an apparatus including an electrode, said method comprising: positioning said electrode substantially adjacent to said foreign material; and creating a channel within said foreign material using said electrode energized with said radiofrequency current to deliver energy into said foreign material to allow the apparatus to be advanced through the channel thereby crossing the septum to be positioned into the left side of the heart.

In accordance with another broad aspect, some embodiments of the present invention provide a method for creating a channel through a foreign material located in a body of a patient, said foreign material defining a material first surface and a substantially opposed material second surface, said channel extending through said foreign material between said material first and second surfaces, said method using an apparatus including an electrode, said method comprising: positioning said electrode substantially adjacent to said material first surface; energizing said electrode with a radiofrequency current; using said electrode energized with said radiofrequency current to deliver energy into said foreign material to create said channel; assessing a composition of a material in contact with said apparatus; and upon determining that said electrode is positioned adjacent a metallic structure, repositioning the apparatus away from said metallic structure.

Many other methods and particular applications may be used with an apparatus of the present invention, and some embodiments of the method of the present invention may be used with an apparatus other than that specifically described in the "APPARATUS" section of this application.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present invention has been described hereinabove by way of preferred embodiments thereof, it can be modified, without departing from the scope and nature of the subject invention as defined in the appended claims.

What is claimed is:

1. A method for creating a channel through a foreign material located in a body of a patient, said foreign material defining a material first surface and a substantially opposed material second surface, said channel extending through said foreign material between said material first and second surfaces, said method using an apparatus including an electrode, said method comprising:
   positioning said electrode substantially adjacent to said material first surface;
   energizing said electrode with a radiofrequency current; and
   using said electrode energized with said radiofrequency current to deliver energy into said foreign material to create said channel;
   wherein said body includes a heart defining a septum, said septum comprising an aperture extending there-through and wherein said foreign material extends across the aperture to cover the aperture.

2. The method of claim 1, wherein said foreign material is included in a septal patch that covers the aperture.

3. The method of claim 2, wherein the septal patch extends in a plane outside of the septum.

4. The method of claim 2, wherein the septal patch extends inside the aperture.

5. The method of claim 1, wherein said septum comprises an atrial septum.

6. The method of claim 1, wherein said septum comprises a ventricular septum.

7. The method of claim 1, wherein said foreign material includes a material selected from the group consisting of polyethylene terephthalate (PET), a cotton, a polyester material and fabrics thereof.

8. The method of claim 7, wherein said foreign material includes a synthetic material.

9. The method of claim 8, wherein said synthetic material comprises a polyester material.

10. The method of claim 1, wherein thermal energy is transferred from said electrode upon said electrode being energized with said radiofrequency current to substantially melt said foreign material adjacent said electrode, thereby creating a channel through said foreign material, wherein said electrode is heated to a temperature that is substantially larger than a melting temperature of said foreign material.

11. A method of gaining access into a left side of a heart, the heart having a septum defining an aperture, wherein foreign material extends across the aperture, said method using an apparatus including an electrode, said method comprising:
   positioning said electrode substantially adjacent to said foreign material; and
   creating a channel within said foreign material using said electrode energized with said radiofrequency current to deliver energy into said foreign material to allow the apparatus to be advanced through the channel thereby crossing the septum to be positioned into the left side of the heart.

12. The method of claim 11, wherein the step of positioning said electrode further comprises gaining access into the heart via an inferior vena cava.

13. The method of claim 11, wherein the step of positioning said electrode further comprises gaining access into the heart via a superior vena cava.

14. A method for creating a channel through a foreign material located in a body of a patient, said foreign material defining a material first surface and a substantially opposed material second surface, said channel extending through said foreign material between said material first and second surfaces, said method using an apparatus including an electrode, said method comprising:

positioning said electrode substantially adjacent to said material first surface;

energizing said electrode with a radiofrequency current;

using said electrode energized with said radiofrequency current to deliver energy into said foreign material to create said channel;

assessing a composition of a material in contact with said apparatus; and upon determining that said electrode is positioned adjacent a metallic structure, repositioning the apparatus away from said metallic structure.

15. The method of claim 14, wherein the steps of assessing and repositioning the apparatus comprise:

measuring an impedance of the material in contact with said apparatus;

determining if the measured impedance indicates that said apparatus is in contact with a metallic structure; and repositioning the apparatus upon determining that said apparatus is in contact with a metallic structure, while repeating the steps of measuring and determining until an impedance is recorded indicating that said apparatus is positioned away from said metallic structure.

16. The method of claim 14, wherein the step of assessing the composition comprises obtaining tactile feedback.

17. The method of claim 14, wherein the step of assessing the composition comprises measuring one or more parameters substantially while delivering energy.

18. The method of claim 15, wherein the impedance is measured substantially continuously during energy delivery.

19. The method of claim 15, wherein the impedance is measured at predetermined intervals during energy delivery.

20. The method of claim 15, wherein the delivery of energy is changed based on a change in the measured impedance.

21. The method of claim 15, wherein the delivery of energy using said electrode is stopped prior to repositioning the apparatus.

\* \* \* \* \*